(12) United States Patent
Kohn

(10) Patent No.: US 9,752,166 B2
(45) Date of Patent: Sep. 5, 2017

(54) PROCESS AND COMPOSITION FOR PRODUCTION OF ORGANIC PRODUCTS

(71) Applicant: Richard Allen Kohn, Columbia, MD (US)

(72) Inventor: Richard Allen Kohn, Columbia, MD (US)

(*) Notice: Subject to any disclaimer, the term of this patent is extended or adjusted under 35 U.S.C. 154(b) by 0 days.

(21) Appl. No.: 14/995,132

(22) Filed: Jan. 13, 2016

(65) Prior Publication Data

US 2016/0145658 A1     May 26, 2016

Related U.S. Application Data

(63) Continuation of application No. 14/214,998, filed on Mar. 16, 2014, now Pat. No. 9,290,734, which is a (Continued)

(51) Int. Cl.
| | |
|---|---|
| *C12P 7/06* | (2006.01) |
| *C12P 7/64* | (2006.01) |
| *C12N 1/20* | (2006.01) |
| *C12R 1/01* | (2006.01) |
| *C12P 7/40* | (2006.01) |
| *C12R 1/19* | (2006.01) |
| *C12R 1/185* | (2006.01) |
| *C12R 1/22* | (2006.01) |
| *C12R 1/42* | (2006.01) |
| *C12P 7/04* | (2006.01) |
| *C12P 7/16* | (2006.01) |
| *C12P 7/44* | (2006.01) |

(Continued)

(52) U.S. Cl.
CPC ............ *C12P 7/6409* (2013.01); *C12N 1/20* (2013.01); *C12P 7/04* (2013.01); *C12P 7/065* (2013.01); *C12P 7/16* (2013.01); *C12P 7/40* (2013.01); *C12P 7/44* (2013.01); *C12P 7/46* (2013.01); *C12P 7/48* (2013.01); *C12P 7/52* (2013.01); *C12P 7/54* (2013.01); *C12R 1/01* (2013.01); *C12R 1/185* (2013.01); *C12R 1/19* (2013.01); *C12R 1/22* (2013.01); *C12R 1/42* (2013.01); *Y02E 50/10* (2013.01); *Y02E 50/17* (2013.01)

(58) Field of Classification Search
CPC ........................................... C12P 7/065
See application file for complete search history.

(56) References Cited

U.S. PATENT DOCUMENTS

| | | |
|---|---|---|
| 5,173,429 A | 12/1992 | Gaddy |
| 5,593,886 A | 1/1997 | Gaddy |

(Continued)

FOREIGN PATENT DOCUMENTS

| | | |
|---|---|---|
| WO | PCTUS2011021436 A1 | 7/2011 |
| WO | PCTUS2012116338 A1 | 8/2012 |

OTHER PUBLICATIONS

Lovitt, R. W., R. Longin, and J. G. Zeikus. Ethanol prouction by thermphilic bacteria: physiological comparison of solvent effects on parent and alcohol-tolerant strains fo Clostridium thermohydrosulfuricum. Applied Environmental Microbiology, Jul. 1984. vol. 48 (1) pp. 171-177.

(Continued)

*Primary Examiner* — Rosanne Kosson

(57) ABSTRACT

The present invention comprises a process to produce organic products from a single-carbon substrate; microbial compositions used in the process; and a process to isolate microorganisms for the process.

19 Claims, 3 Drawing Sheets

Related U.S. Application Data continuation-in-part of application No. 14/869,207, filed on Sep. 29, 2015, which is a continuation of application No. 13/381,127, filed as application No. PCT/US2010/058959 on Dec. 3, 2010, now Pat. No. 9,217,161.

(60) Provisional application No. 61/794,509, filed on Mar. 15, 2013, provisional application No. 61/328,368, filed on Apr. 27, 2010, provisional application No. 61/266,610, filed on Dec. 4, 2009.

(51) Int. Cl.
| | |
|---|---|
| *C12P 7/46* | (2006.01) |
| *C12P 7/48* | (2006.01) |
| *C12P 7/52* | (2006.01) |
| *C12P 7/54* | (2006.01) |

(56) References Cited

U.S. PATENT DOCUMENTS

| | | | |
|---|---|---|---|
| 6,136,577 | A | 10/2000 | Gaddy |
| 7,285,402 | B2 | 10/2007 | Gaddy |
| 8,178,329 | B2 | 5/2012 | Kohn |
| 8,349,587 | B2 | 1/2013 | Fischer |
| 8,535,921 | B2 | 9/2013 | Kohn |
| 8,759,070 | B2 | 6/2014 | Papoutsakis |
| 9,051,552 | B2 | 6/2015 | Burk |
| 9,121,040 | B2 | 9/2015 | Kohn |
| 9,193,979 | B2 | 11/2015 | Kohn |
| 2008/0176301 | A1 | 7/2008 | Granda |
| 2010/0120106 | A1 | 5/2010 | Kohn |
| 2011/0003344 | A1 | 1/2011 | Burk |
| 2012/0100591 | A1 | 4/2012 | Kohn |
| 2013/0052689 | A1 | 2/2013 | Banta |
| 2013/0130341 | A1 | 5/2013 | Liao |
| 2014/0087436 | A1 | 3/2014 | Tabita |
| 2014/0148621 | A1 | 5/2014 | Kohn |

OTHER PUBLICATIONS

Henstra, A. M., J. Sipma, A. Rinzema, A. J. M. Stams. "Microbiology of synthesis gas fermentation for biofuel production." Current Opinion in Biotechnology, Jun. 2007, vol. 18 (3) pp. 200-206.

Younesi, H., G. Najafpour, A. R. Mohamed. "Ethanol and acetate production from synthesis gas via fermentation processes using anaerobic bacterium, Clostridium ljungdahili" Biochemical Engineering Journal, Dec. 2005, vol. 27 (2) pp. 110-119.

Klasson, K. T., M. D. Ackerson, E. C. Clausen, J. L. Gaddy. "Bioreactors for synthesis gas fermentations" Resources, Conservation and Recycling. Apr. 1991, vol. 5: (2-3) pp. 145-165.

Klasson, K. T., M. D. Ackerson, E. C. Clausen, J. L. Gaddy. "Bioconversion of synthesis gas into liquid or gaseous fuels" Enzyme and Microbial Technology, Aug. 1992. vol. 14: (8) 602-608.

Lan, E.I., J. C. Liao. "Metabolic engineering of cyanobacteria for 1-butanol production from carbon dioxide", Metabolic Engineering (May 2011) vol. 13, pp. 353-363.

Fischer, C. R., D.Klein-Marcuschamer, G. Stephanopoulos. "Selection and optimization of microbial hosts for biofuels production" Metabolic Engineering, Nov. 2008, vol. 10 (6) pp. 295-304.

Atsumi, S., A. F. Cann, M. R. Connor, C. R. Shen, K. M. Smith, M. P. Brynildsen. "Metabolic engineering of *Escherichia coli* for 1-butanol production" Metabolic Engineering, Nov. 2008. vol. 10(6) 305-311.

Atsumi, S., T. Flanai, and J. C. Liao. "Non-fermentative pathways for synthesis of branched-chain higher alcohols as biofuels". Nature. (Jan. 2008) vol. 451:pp. 86-89.

Pind,P. "Dynamics of the anaerobic process: effects of volatile fatty acids", Biotechnology and Bioengineering. (Jun. 30, 2003). vol. 82: (7) pp. 791-801.

Bond-Watts, B. B., R. J. Bellerose, and M. C. Y. Chang. "Enzyme mechanism as a kinetic control element for designing synthetic biofuel pathways", Nature Chemical Biology, (Feb. 27, 2011). vol. 7, pp. 222-227.

Sahin, A., W.-T. Lin, W. O. Khunjar, K. Chandran, S. Banta, and A. C. West. "Electrochemical Reduction of Nitrite to Ammonia for Use in a Bioreactor", Journal of the Electrochemical Society, ( Nov. 7, 2012) vol. 160 (1) pp. G19-G26.

Li, H., P. H. Opgenorth, D. G. Wernick, S. Rogers, T. Y. Wu, W. Higashide, P. Malati, Y. X. Huo, K. M. Cho, J. C. Liao. "Integrated electromicrobial converson of CO2 to higher alcohols", Science (Mar. 30, 2012) vol. 335 (6076) pp. 1596.

```
                       SEQUENCE LISTING

<160> NUMBER OF SEQ ID NOS: 5

<210> SEQ ID NO 1
<211> LENGTH: 581
<212> TYPE: DNA
<213> ORGANISM: unknown
<220> FEATURE:
<223> OTHER INFORMATION: PCR-derived 16s rRNA gene, highly homologous to
      multiple bacteria.

<400> SEQUENCE: 1
gctgcttcgc tgacgagtgg cggacgggtg agtaatgtct gggaaactgc ctgatggagg      60
gggataacta ctggaaacgg tagctaatac cgcataacgc cgcaagacca aagaggggga    120
gcttcgggcc tcttgccatc agatgtgccc agatgggatt agcttgttgg tggggtaacg    180
gctcaccaag gcgacgatcc ctagctggtc tgagaggatg accagccaca ctggaactga    240
gacacggtcc agactcctac gggaggcagc agtggggaat attgcacaat gggcgcaagc    300
ctgatgcagc catgccgcgt gtatgaagaa ggccttcggg ttgtaaagta ctttcagcgg    360
ggaggaaggt gttgtggtta ataaccgcag caattgacgt tacccgcaga agaagcaccg    420
gctaactccg tgccagcagc cgcggtaata cggagggtgc aagcgttaat cggaattact    480
gggcgtaaag cgcacgcagg cggtctgtta agtcagatgt gaaatccccg ggctcaacct    540
gggaactgca tctgatactg gcaggcttga gtctcgtaga g                        581

<210> SEQ ID NO 2
<211> LENGTH: 552
<212> TYPE: DNA
<213> ORGANISM: unknown
<220> FEATURE:
<223> OTHER INFORMATION: PCR-derived 16s rRNA gene, highly homologous to
      multiple bacteria.
<220> FEATURE:
<221> NAME/KEY: misc_feature
<222> LOCATION: (536)..(536)
<223> OTHER INFORMATION: n is a, c, g, or t

<400> SEQUENCE: 2
tgagtaatgt ctgggaaact gcctgatgga gggggataac tactggaaac ggtagctaat     60
accgcataac gtcgcaagac caaagagggg gaccttcggg cctcttgcca tcggatgtgc    120
ccagatggga ttagcttgtt ggtggggtaa cggctcacca aggcgacgat ccctagctgg    180
tctgagagga tgaccagcca cactggaact gagacacggt ccagactcct acgggaggca    240
gcagtgggga atattgcaca atgggcgcaa gcctgatgca gccatgccgc gtgtatgaag    300
```

```
aaggccttcg ggttgtaaag tactttcagc ggggaggaag gtgttgaggt taataacttt    360
gccaattgac gttacccgca gaagaagcac cggctaactc cgtgccagca gccgcggtaa    420
tacggagggt gcaagcgtta atcggaatta ctgggcgtaa agcgcacgca ggcggttttgt   480 taagtcagat gtgaaatccc cgggctcaac ctgggaactg catctgatac tggcangctt    540
gagtctcgta ga                                                         552
```

<210> SEQ ID NO 3
<211> LENGTH: 888
<212> TYPE: DNA
<213> ORGANISM: Unknown
<220> FEATURE:
<223> OTHER INFORMATION: PCR-derived 16s rRNA gene, highly homologous to multiple bacteria.

<400> SEQUENCE: 3

```
gggcggtgtg tacaaggccc gggaacgtat tcaccgtggc attctgatcc acgattacta     60
gcgattccga cttcatggag tcgagttgca gactccaatc cggactacga catactttat    120
gaggtccgct tgctctcgcg aggtcgcttc tctttgtata tgccattgta gcacgtgtgt    180
agccctactc gtaagggcca tgatgacttg acgtcatccc caccttcctc cagtttatca    240
ctggcagtct cctttgagtt cccgaccgaa ccgctggcaa caaaggataa gggttgcgct    300
cgttgcggga cttaacccaa catttcacaa cacgagctga cgacagccat gcagcacctg    360
tctcagagtt cccgaaggca ccaaagcatc tctgctaagt tctctggatg tcaagagtag    420
gtaaggttct tcgcgttgca tcgaattaaa ccacatgctc caccgcttgt gcgggccccc    480
gtcaattcat ttgagtttta accttgcggc cgtactcatg tctgggaaac tgcccgatgg    540 aggggggataa ctactggaaa cggtagctaa taccgcataa cgtcgcaaga ccaaagaggg    600
ggaccttcgg gcctcttgcc atcggatgtg cccagatggg attagctagt aggtggggta    660
acggctcacc taggcgacga tccctagctg gtctgagagg atgaccagcc acactggaac    720
tgagacacgg tccagactcc tacgggaggc agcagtgggg aatattgcac aatgggcgca    780
agcctgatgc agccatgccg cgtgtatgaa gaaggccttc gggttgtaaa gtactttcag    840
cgaggaggaa ggtgttgtgg ttaataaccg cagcgattga cgttactc                 888
```

<210> SEQ ID NO 4
<211> LENGTH: 458
<212> TYPE: DNA
<213> ORGANISM: Unknown
<220> FEATURE:
<223> OTHER INFORMATION: PCR-derived 16s rRNA gene, highly homologous to multiple bacteria.

<400> SEQUENCE: 4

```
tccgtggatg tcaagaccag gtaaggttct tcgcgttgca tcgaattaaa ccacatgctc     60
caccgcttgt gcgggccccc gtcaattcat ttgagtttta accttgcggc cgtactcccc    120
aggcggtcga cttaacgcgt tagctccgga agccacgcct caagggcaca acctccaagt    180
cgacatcgtt tacggcgtgg actaccaggg tatctaatcc tgtttgctcc ccacgctttc    240
gcacctgagc gtcagtcttc gtccagggggg ccgccttcgc caccggtatt cctccagatc    300
tctacgcatt tcaccgctac acctggaatt ctaccccccct ctacgagact caagcctgcc    360
agtatcagat gcagttccca ggttgagccc ggggatttca catctgactt aacagaccgc    420
ctgcgtgcgc tttacgccca gtaattccga ttaacgct                             458
```

```
-continued

<210> SEQ ID NO 5
<211> LENGTH: 444
<212> TYPE: DNA
<213> ORGANISM: Unknown
<220> FEATURE:
<223> OTHER INFORMATION: PCR-derived 16s rRNA gene, highly homologous to
      multiple bacteria.

<400> SEQUENCE: 5
cggctaacta cgtgccagca gccgcggtaa tacgtaggtg gcaagcgttg tccggattta      60
ttgggcgtaa agcgagcgca ggcggtttct taagtctgat gtgaaagccc ccggctcaac    120
cggggagggt cattggaaac tgggagactt gagtgcagaa gaggagagtg gaattccatg    180
tgtagcggtg aaatgcgtag atatatggag gaacaccagt ggcgaaggcg gctctctggt    240
ctgtaactga cgctgaggct cgaaagcgtg gggagcaaac aggattagat accctggtag    300
tccacgccgt aaacgatgag tgctaagtgt tggagggttt ccgcccttca gtgctgcagc    360
aaacgcatta agcactccgc ctggggagta cgaccgcaag gttgaaactc aaaggaattg    420 acggggccc gcacaagcgg tgga                                            444
```

PROCESS AND COMPOSITION FOR PRODUCTION OF ORGANIC PRODUCTS

RELATED APPLICATIONS

This application is a continuation of U.S. patent application Ser. No. 14/214,998 filed on Mar. 16, 2014, which claims priority to U.S. Provisional Application No. 61/794,509 filed on Mar. 15, 2013. This application is also a continuation-in-part application of U.S. patent application Ser. No. 14/869,207 filed on Sep. 29, 2015, which is a continuation of U.S. patent application Ser. No. 13/381,127 filed on Dec. 28, 2011, now U.S. Pat. No. 9,217,161, which is a national stage entry of PCT/US10/058,959 filed on Dec. 3, 2010, which claims priority to U.S. Provisional Application No. 61/328,368 filed on Apr. 27, 2010 and U.S. Provisional Application No. 61/266,610 filed on Dec. 4, 2009.

BACKGROUND OF THE INVENTION

Field of the Invention

The present invention relates to a process for producing organic compounds such as lower alkyl alcohols, including ethanol, propanol (e.g. 1-propanol, iso-propanol), and butanol (e.g. 1-butanol, 2-butanol, 3-butanol, and iso-butanol) from gases including carbon dioxide, carbon monoxide, and hydrogen under thermodynamically favorable conditions; microorganisms used in the process to produce organic compounds from gases; and a process for enriching, isolating, and improving microorganisms that can be used in the process to produce organic compounds from gases. The process may also be used to produce one or more carboxylic acids including acetic acid, propionic acid, or butyric acid, other carboxylic acids, especially longer carboxylic acids, and the process produces animal feeds, and can be used to produce other products.

Background

Previous inventors have disclosed methods for conversion of synthesis gases ($CO_2$, CO and $H_2$) to lower alkyl alcohols or organic acids (For example, U.S. Pat. Nos. 5,173,429; 5,593,886; and 6,136,577, which are incorporated herein by reference). These methods use microorganisms that are fastidious and strictly anaerobic and do not tolerate high concentrations of alcohols or acids. These microorganisms have complex nutrient requirements (fastidious) or they grow very slowly or are difficult to maintain for industrial processes. For example, strictly anaerobic microorganisms do not grow, or may be killed, if exposed to even minute concentrations of oxygen. Fastidious microorganisms may require addition of growth factors that increase the cost of the process.

Aerotolerant microorganisms such as strains of *Enterococcus* species have been isolated and shown to also take up $CO_2$, CO and $H_2$, and convert these gases to lower alkyl alcohols or organic acids. For example, see the previous patent by the inventor of the present disclosure (U.S. Pat. No. 8,178,329; issued May 15, 2012), which is incorporated herein in its entirety by reference. Isolated strains of *Enterococcus* species produced mostly alcohols under certain conditions, and produced various acids under other conditions. They could also tolerate high concentrations of the acids and alcohols. However, even with *Enterococcus* species, exogenous sources of carbon such as amino acids or yeast extract were used. The inventor also disclosed isolated organisms and processes to make hydrocarbons like $C_2$-$C_{10}$ alkanes in U.S. patent application Ser. No. 13/381,127 filed on Dec. 28, 2011, which is incorporated herein in its entirety by reference. The genera of isolated microbes that made alkanes included *Escherichia* and *Proteus* among others, but the alkane-producing isolates had not been selected for the ability to grow on single-carbon substrates.

SUMMARY

Therefore, the present invention improves upon these previous processes by using microbial cultures that grow rapidly, tolerate high concentrations of lower alkyl alcohols and organic acids, and can produce lower alkyl alcohols and organic acids from $CO_2$ or CO as the only (sole) carbon source. Using the microbial compositions described in this disclosure, along with the disclosed conditions, makes it possible to produce high concentrations of organic products from single carbon compounds.

The isolated microorganisms used in the process to produce organic products are one embodiment of the invention.

In one embodiment the isolated microorganisms can grow using carbon dioxide or carbon monoxide as the sole carbon source. These organisms do not need to be supplemented with organic growth factors such as amino acids or vitamins. In addition, these isolated microorganisms may be chemoautotrophic and non-photosynthetic and grow without light. Preferably, the isolated microorganisms are tolerant to lower alkyl alcohols and/or organic acids. Several isolated species are members of the family Enterobacteriaceae.

In another embodiment the isolated microorganisms are aerobic microorganisms that grow rapidly from degradation of organic compounds under aerobic conditions, but can use $CO_2$ or CO under reducing conditions to fix the carbon to form multi-carbon compounds and produce organic products. Preferably, the isolated microorganisms are chemoautotrophic and non-photosynthetic and grow without light, and are tolerant to organic products they produce.

In still yet another embodiment, the isolated microorganisms comprise both traits: ability to grow using carbon dioxide or carbon monoxide as the sole carbon source, and ability to grow from degradation of organic compounds under conditions favoring degradation of the compounds. Under reducing conditions, the organisms produce organic products such as lower alkyl alcohols or organic acids. Several isolated species were members of the family Enterobacteriaceae.

One group of isolated chemoautotrophic bacteria that can grow using carbon dioxide or carbon monoxide as the sole carbon source are facultative aerobic and grow rapidly under aerobic conditions, tolerate high concentrations of lower alkyl alcohols and organic acids, and they produce organic products. The products they produce include lower alkyl alcohols (a.k.a. $C_2$-$C_5$ alkyl alcohols) such as ethanol, propanol (e.g. 1-propanol, iso-propanol), and butanol (e.g. 1-butanol, 2-butanol, isobutanol). The organisms tolerate high concentrations of lower alkyl alcohol such as at least 0.5%, 1%, 2%, 3%, 4%, 5%, 6%, or greater lower alkyl alcohol volume per volume of fermentation broth (v/v). The organisms also tolerate high concentrations of organic acids and produce organic acids such as acetic acid, propionic acid, lactic acid, butyric acid, succinic acid, iso-butyric acid, valeric acid, isovaleric acid, and others.

Example isolated microorganisms include species from the genera: *Citrobacter, Klebsiella, Escherichia, Salmonella*, and *Enterobacter*, among others. For example, biochemical classification and 16S rRNA identified the isolated microorganisms as bacteria belonging to the species *Citrobacter koseri, Klebsiella oxytoca*, and *Escherichia coli*, among others. All of these species are phylogenetically related as members of the Enterobacteriaceae family, and multiple independent isolation procedures produced several different strains of several of these genera that met the criteria that comprise an aspect of the invention.

Additional microorganisms are also used in the invented process and isolates of them are an additional aspect of the invention. These isolates thrive when amino acids, peptides or true proteins are present in the medium, and they can use $CO_2$ or CO to produce alcohols and acids, and they are also tolerant to high concentrations of alcohols (e.g. up to more than 10% ethanol by volume) and acids (e.g. up to more than 50 g acetate per liter of fermentation broth). These additional microorganisms include members of the genus *Enterococcus*, such as *E. gallum, E. faecalis, E. faecium, E. durans, E. casselflavus*, and several *Clostridium* species.

One embodiment of the invention is a process to ferment carbon dioxide ($CO_2$) or bicarbonate ($HCO_3^-$) and a chemical reducing agent to lower alkyl alcohol or organic acid. Another embodiment of the invented process is to ferment carbon monoxide (CO) or formate, wherein the carbon source is also a reducing agent to produce lower alkyl alcohol or organic acid. Carbon monoxide and formate are produced as intermediates in anaerobic ecosystems that reduce $CO_2$, thus CO or formate can also be added as substrates for the process bypassing initial steps for reducing $CO_2$.

For fermentation of $CO_2$ or $HCO_3^-$ to lower alkyl alcohol or carboxylic acid, the chemical reducing agent can be hydrogen ($H_2$), or other chemical such as reduced a metal (e.g. Cu, Fe, Mn) or reduced sulfur compound (e.g. sulfide, $S^{2-}$), or electrons (hydrogen equivalent) provided by an electrode with electricity. Alternatively, the CO or formate can act as both reducing agent and source of carbon, but additional reducing agent (e.g. $H_2$, sulfide, electrons) can be added.

The lower alkyl alcohol produced in the process may be ethanol, or a propanol (e.g. 1-propanol, iso-propanol), or a butanol (e.g. 1-butanol, iso-butanol), or other. The volume of ethanol can reach at least 10% of the volume of fermentation broth, or propanols or butanols can reach at least 6% of the volume of the fermentation broth. The volume of ethanol as a percentage of the volume of fermentation broth can be at least 1%, 2%, 3%, 4%, 5%, 6%, 7%, 8%, 9% or 10%, and the volumes of $C_3$-$C_4$ alcohols (e.g. propanol and/or butanol) can be at least 0.5%, 1%, 2%, 3%, 4%, 5%, or 6% of the fermentation broth volume. The carboxylic acid may be acetic acid, propionic acid, lactic acid, butyric acid, isobutyric acid, succinic acid, valeric acid, isovaleric acid, caproic acid, citric acid, malic acid, or fumaric acid or other acid. The carboxylic acids are maintained in solution mainly in the conjugate base form, and may comprise at least 1%, 2%, 3%, 4%, 5%, 6%, or more of the fermentation broth by weight of acid (including conjugate base form) to volume of fermentation broth (i.e. grams conjugate base and acid per 100 ml fermentation broth, w/v). The concentrations of acids may equivalently be expressed as 10, 20, 30, 40, 50, 60 g or more acid in both conjugate base and acid form per L volume of fermentation broth, i.e. 10 g/L equals 1% (w/v) of acid.

In one embodiment of the invented process, $CO_2$ or CO gas is fermented to organic compounds using aerobic microorganisms and/or microorganisms that can use $CO_2$ or CO as their sole carbon source. A combination of microbial species may be used.

Aerobic microorganisms including members of the Enterobacteriaceae such as members of the genera *Citrobacter, Klebsiella, Escherichia*, and *Enterobacter* were discovered to harbor advantageous traits for use in a process to produce lower alkyl alcohol or organic acid from single-carbon compounds like $CO_2$, $HCO_3^-$, or CO. It is also advantageous to use non-aerobic but aerotolerant organisms, meaning they tolerate oxygen, such as *Enterococcus*. The aerobic and aerotolerant organisms make the fermentation anaerobic to support the growth or survival of strict anaerobic species like members of the genus *Clostridium*. Additionally, even aerobic organisms reduce carbon compounds to make desired products more efficiently once the fermentation broth becomes anaerobic. Therefore, one embodiment of the present invention is to include aerobic microorganisms that are tolerant to the desired products in a fermentation to produce desired products from single carbon compounds. Preferably, the tolerant microorganisms also make the desired products from the single carbon compounds under reducing conditions.

The use of non-fastidious organisms that can grow without amino acids or yeast extract enables the growth of microorganisms and product formation without the addition of expensive growth factors to the media. The fastidious organisms can obtain nutrients from the non-fastidious organisms. Thus, another embodiment of the invention is a process of including non-fastidious organisms that can grow on carbon dioxide or carbon monoxide as a sole carbon source into a fermentation to produce desired organic products from single carbon compounds. Organisms such as members of the Enterobacteriaceae family including the genera *Citrobacter, Klebsiella, Escherichia*, and *Enterobacter* are non-fastidious and are excellent candidates for inclusion. These organisms provide an additional benefit by being aerobic. A consortium of microorganisms is more stable and may be most effective at producing desired organic products than mono-cultures, and one embodiment of the invention is to use such a consortium of microorganisms.

The invented process to produce lower alkyl alcohols or organic acids may comprise different steps: a biomass-degrading step, and a reducing step in which the microorganisms convert the $CO_2$ or CO to the desired lower alkyl alcohol or acid. The biomass-degrading step may be aerobic or anaerobic using organic substrate for energy. The reducing step where the $CO_2$ or CO are used to make the desired product may be anaerobic, or may become anaerobic from metabolism of the microorganisms. Optionally, the same microorganisms can be used in both steps. Exogenous reducing agents may be added in the reducing step. Reducing agents may include $H_2$, sulfide, electrons from an electrode, reduced metals, CO, or formate. In addition, a simple carbon source such as $CO_2$, $HCO_3^-$, CO, or formate may be supplied in the reducing step. The carbon source, e.g. $CO_2$, may come from the biomass-degrading step from degradation of biomass or other substrate to $CO_2$. In the reducing step, fermentation of $CO_2$, $HCO_3^-$, CO, or formate under reducing conditions causes the microorganisms to produce the desired products. The desired products may be removed after the reducing step, and the microorganisms and the other products and liquids returned to the biomass-degrading step in which the microorganisms may be rapidly grown. The co-products from the reducing step, which may not be as desired, may provide organic substrate for growth of additional organisms, and production of additional desired product and $CO_2$. The steps may even occur at the same time, or may occur in sequence, in the same reactor under different conditions, or in different reactors.

In one embodiment of the invention, microorganisms could also use glucose, citrate, alcohols, acids, cellobiose or plant fiber (e.g. ligno-cellulose, hemicellulose) and grow under aerobic conditions producing $CO_2$, or convert the glucose, citrate, cellobiose, or plant fiber to acids and alcohols under anaerobic conditions. The reducing step uses pressures and concentrations of gases to make it thermodynamically favorable to produce the alcohols or acids from the gases, and under those conditions the alcohols and acids are produced to desired concentrations by the process. Organisms preferentially convert biomass (e.g. plant fiber) to the higher concentrations of alcohols or acids, particularly longer chain acids, when the gas pressures and compositions are increased to thermodynamically favor conversion to these products over conversion to gases themselves. Many other types of organisms could also be used in the process. Thus, one embodiment of the invention is a process in which substrates are degraded under one set of conditions, such as low hydrogen pressures or aerobic conditions, and the gases are synthesized into desired products under a different set of conditions, such as anaerobic, reducing conditions, optionally under greater than 1 atm pressure. Another embodiment of the invention is the undesired co-products produced from the reducing conditions are recycled to the biomass-degrading conditions to produce more intermediates for further product formation One aspect of the process that embodies the invention is that aerobic microorganisms may use oxygen and make the fermentation broth more anaerobic to aid in the growth of strict anaerobic microorganisms like Clostridial species that use CO, or $CO_2$ and $H_2$, to produce organic products. The aerobic microorganisms, which are able to grow on CO or $CO_2$ as the sole substrate, may also be digested or may release complex organic substrates such as amino acids or vitamins that can be used by the more fastidious organisms in the culture. Thus, one aspect of the invention is to include aerobic microorganisms that use $O_2$ and maintain anaerobic conditions, but also do not degrade desired products under the process conditions, but may make additional products. These added aerobic microorganisms preferably are tolerant to high concentrations of the desired products.

Thus, the present invention comprises a process to rapidly grow microorganisms optionally under aerobic conditions, and preferably using unwanted organic substrates from a reducing step. The process also preferably comprises using the same rapidly grown microorganisms to readily produce organic products by fermentation of $CO_2$ or CO in the reducing step.

Products from the process, including organic acids and bacteria themselves, can be used in feed for ruminants or other animals.

The invention also comprises a method to enrich for or isolate aerobic microorganisms that ferment $CO_2$ or CO to desired organic compounds, and a process to enrich for and isolate microorganisms that can grow solely on the carbon from $CO_2$ or CO.

The process of enrichment for aerobic microorganisms comprises a step of growing an environmental source of microorganisms under aerobic conditions using a desired product as substrate. For example, organisms can be grown aerobically on alcohols, either as a mixture or individually, including ethanol, propanol, butanol, pentanol, or other alcohol, or the microbes can be grown aerobically on organic acids such as acetate, propionate, butyrate, isobutyrate, succinate, valerate, isovalerate, citrate, caproic acid, capric acid, etc. The process can readily be used for other organic substrates as well. Microorganisms have evolved to degrade all organic substrates on earth.

An embodiment of the disclosed in invention is a process to enrich and isolate microorganisms that grow in high concentrations of desired lower alkyl alcohol or organic acids and are either facultative aerobic, or can grow on CO or $CO_2$ as a sole carbon source, or both. This process comprises growing a mixed culture of microorganisms in a broth or agar media with one or more lower alkyl alcohols at a high concentration (e.g. 0.5%, 1%, 2%, 3%, 4%, 5%, 6%, 7%, 10%, or higher by volume), or with one or more organic acids at a high concentration (e.g. 0.5%, 1%, 2%, 3%, 4%, 5%, or 6% by weight per volume), and growing the culture in aerobic stages favoring degradation of the alcohols or acids to $CO_2$ and $H_2$, and/or limiting carbon in the medium to the alcohol or acid to select for organisms that can grow without amino acids or vitamins. Alternatively, the cultures are grown anaerobically with high pressures of CO, or $H_2$ and $CO_2$, or other reducing agent and carbon source. For example, 2 to 8 atm pressure with ratio of $H_2:CO_2$ greater than 1:1 can be used.

One embodiment of the invention is enriching or isolating microorganisms by growing them under aerobic conditions favoring degradation of the product what will be the eventual desired product as substrate, wherein the eventual desired product is included at a high enough concentration to select for aerobic organisms tolerant to high concentrations of the desired product. The concentrations of the substrates can be varied In an alternative embodiment, the enrichment step can include enriching for microorganisms that grow on broth medium with minerals and a source of nitrogen, but otherwise limited to a substrate comprising only the eventual desired product as a carbon source. This fermentation can be aerobic or anaerobic and can use air, $CO_2$, $N_2$, or other gas in the headspace. However, because amino acid protein or vitamins are not included in the medium, non-fastidious organisms will be enriched for. For example, enriching on media (broth or agar) wherein citrate is the only carbon source selects for limited strains of microorganisms (e.g. *Citrobacter, Klebsiella*).

An additional enrichment or isolation step includes growing the enriched culture of microorganisms on media containing various concentrations of the eventual desired product and high concentrations of $CO_2$ and $H_2$ so that it is thermodynamically feasible to make additional desired product, and thermodynamically infeasible to degrade the desired product in the fermentation broth or agar to $CO_2$ and $H_2$. For example, ratio of $H_2:CO_2$ may be greater than 1:1 and pressures may be greater than 1 atm.

After several enrichment phases, the broth is diluted so the individual cells will be separated with transferring to agar plates. The plates can alternatively provide conditions wherein organisms grow from single-carbon substrates under gas pressures and substrate concentrations that make it thermodynamically favorable to produce the desired product, or the conditions permit them to degrade the desired product. In either case, isolates are transferred to additional media and tested for what products they produce from CO, $CO_2$, $HCO_3^-$, and reducing agents as desired. Isolates with desired product profiles are thereafter used in processes to make the desired products under conditions wherein it is thermodynamically feasible to make the desired products.

DETAILED DESCRIPTION OF THE PREFERRED EMBODIMENTS

Term Definitions

Figure 1:
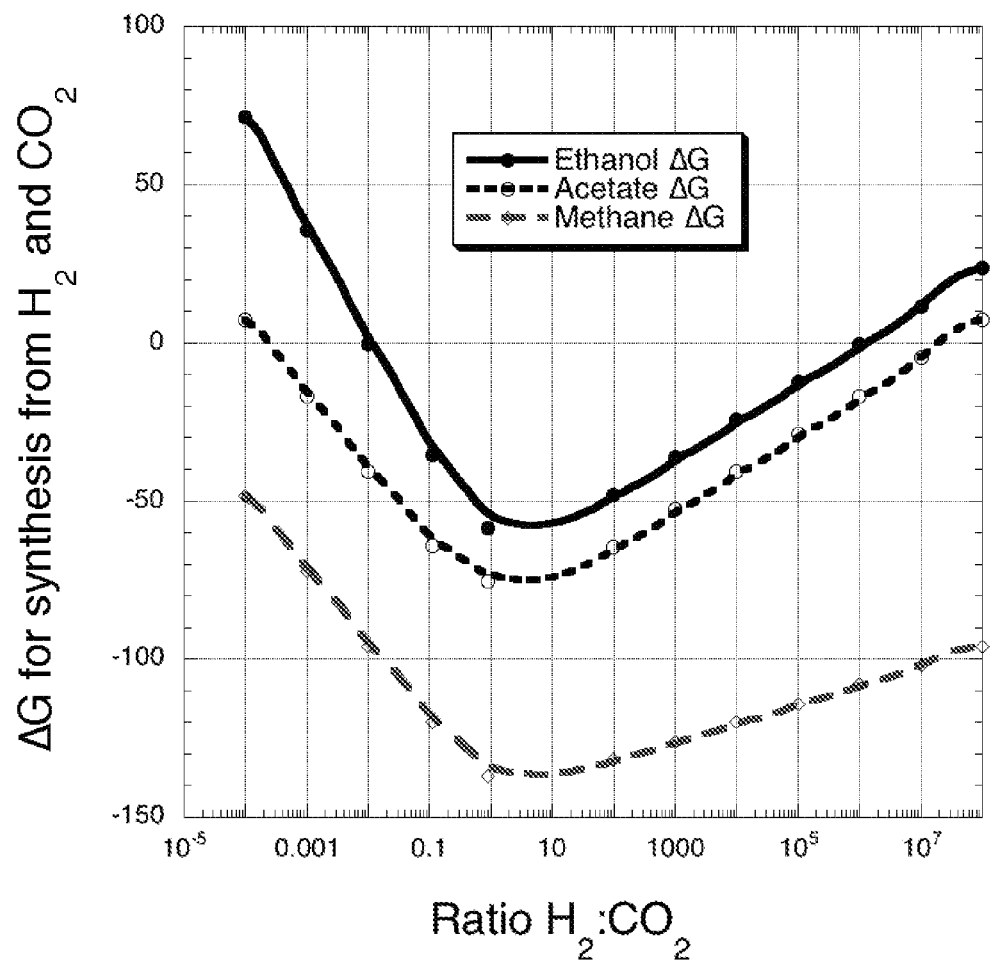
FIG. 1. The change in free energy ($\Delta G$, kJ/mol) for synthesis of ethanol, acetate or methane from $H_2$ and $CO_2$ as the molar ratio of $H_2$ to $CO_2$ increases. This figure shows the energy available for forming different products peaks at a ratio of about 2 to 4.

Aerobic microorganism: means the microorganism has the ability to use oxygen to oxidize substrate for energy.

Aerotolerant: means the microorganism is able to grow in the presence of open air, such as an open flask because oxygen is not toxic to the organism.

Alcohol tolerant: means that the microorganism is able to grow in the presence of alcohols. Generally this means an amount of total alcohols (e.g. ethanol+propanol+butanol+pentanol) of at least about 0.5% to about 1% by volume, and preferably about 2% by volume, even more preferably 3%, 4%, 5%, or 6% alcohol by volume of fermentation broth or agar media.

Autotrophic: means a type of organism that produces complex organic compounds from simple compounds using light or a chemical as an energy source.

Biomass: means material derived from living, or recently living organisms. For the present document, biomass is to be considered organic unless otherwise stated.

Butanol tolerant: means that the microorganism is able to grow in the presence of butanol. Generally, this means an amount of butanol of at least 0.5% to 1% by volume, and preferably about 2%, even more preferably about 3%, 4%, 5%, or 6% by volume of aqueous medium.

Carboxylic acid: means an organic compound containing the carboxyl group COOH or COO$^-$ making it an organic acid because the proton (H$^+$) can be donated. Carboxylic acids range in length from 1 to many carbons, such as greater than 20 carbons. Carboxylic acids are also called organic acids. The short-chain carboxylic acids ($C_2$ to $C_5$) are also called volatile fatty acids (VFA). Carboxylic acids are readily interconverted with their conjugate base (acid having released a proton to solution) in aqueous solutions and thus production of the acid or the base form is considered production of either form as they can be readily interconverted by adjusting pH of the solution.

Chemoautotrophic: means a type of organism that can synthesize its own organic molecules from fixation of carbon dioxide by obtaining energy from inorganic chemicals.

Chemotrophic: means a type of organism that can obtain energy from inorganic chemicals. These are classified into two groups: chemoautotrophs and chemoheterotrophs.

Chemoheterotrophic: means a type of organism that is unable to synthesize its own organic molecules from inorganic substrates (e.g. $CO_2$), but which can obtain energy from inorganic molecules.

Conjugate base: is one of two members of a pair of compounds that can be interconverted by gain or loss of a proton (H$^+$). The conjugate base accepts a proton from solution wherein the conjugate acid donates a proton. For example, for acetic acid the acid form is referred to as the conjugate acid and acetate is referred to as the conjugate base. Near neutral pH (e.g. about 5 to about 7), most acid-base pairs of volatile fatty acids are predominantly in the conjugate base form. Furthermore, when free energy is calculated based on acid and base concentrations, the concentration of conjugate base was used with the associated concentration of protons (H$^+$). A process that produces an acid or its conjugate base and a proton are considered equivalent because the two forms are readily interconverted. In this disclosure, often acids are named in the acid form (e.g. acetic acid, propionic acid), or described as "acids" but would be found as a mixture of acids and conjugate bases and would be mostly in the conjugate base form at neutral pH. For example, a 1% solution of strong acid, like HCl, is nearly all dissociated into the conjugate base form (Cl$^-$) but is still referred to as a solution of hydrochloric acid. Likewise, dilute acids like acetic acid are also nearly all dissociated into the base form at neutral pH (i.e. >5), but are still referred to as dilute acid, and 5% acetic acid means 5 grams of acetic acid form plus acetate form per 100 ml of solution.

Defined cultures: Cultures of microorganisms that have been isolated and at least partially characterized e.g. possibly identified as genus and species, or phylogenetically characterized by sequencing the variable region of 16S rRNA, or by sequencing the complete genome.

Direct evolution: means to direct the development of microorganisms that are well suited, preferably particularly well suited, for a given environment that is different from the environment from which the organism was taken, thereby changing the organism to be better suited to the new environment.

Directed equilibrium: means a process in accordance to the invention in which a system is allowed to move toward equilibrium, but concentrations of reactants and products within the system are manipulated, and possibly some reactions are directly inhibited, to direct the system to produce different products than would otherwise be produced as equilibrium is approached.

Ethanol tolerant: means that a microorganism is able to grow in the presence of ethanol. Generally, this means an amount of ethanol of at least about 0.5% to about 1% ethanol by volume, and preferably about 2%, even more preferably about 3%, 4%, 5%, or 6%, or more by volume of aqueous medium.

Favor: means the concentrations of reactants and products for competing reactions in the system, such as fermentation, are such that a greater decrease in free energy (more negative $\Delta G$) results from one reaction compared to another, where the first reaction is said to be favored over the other or others. For example, synthesis of acetate may be said to be favored over synthesis of ethanol under certain conditions, or alternatively acetate synthesis may be said to be favored over acetate degradation under certain conditions.

Favorable Free Energy for Synthesis: means the change in Gibbs Free Energy ($\Delta G$) is negative for the combination of reactions that comprise the system that converts a set of reactants to a set of products, and the system can therefore convert the reactants to products. The $\Delta G$ is calculated based on the change in Gibbs Free Energy under standard ($\Delta G°$) of temperature and the concentrations or partial pressures of reactants and products. The $\Delta G°$ is calculated as the difference in Gibbs Free Energy of Formation ($\Delta G'_f$) for the products and reactants. The $\Delta G°_f$ is the $\Delta G$ for formation of any material from the elements i.e. graphite, $H_2$, $O_2$, for example, under standard conditions. Standard conditions means standard temperature (298.15 K unless otherwise indicated), 1 molar concentration of all solutes of reactants and products and 1 atmosphere partial pressure of gases combined.

Fermentation or fermentation system: refers to the use of microorganisms to produce a product by, for example, the conversion of infused gases to acetate or ethanol; where the fermentation or the fermentation system refers to the totality of all possible reactions which occur during digestion.

Inorganic: means a chemical element or compound that does not contain carbon bound to other elements, and some additional carbon compounds typically considered inorganic ($CO_2$, CO, carbides, carbonates, and cyanides). In the present specification, $CO_2$, CO, $HCO_3^-$, among others, are to be interpreted as inorganic carbon compounds.

Isolated microorganisms: means one or more microorganisms that either have been isolated from a natural environment and grown in culture, or that have been developed using the methodologies from the present invention and grown in culture. Some are highly pure, originally from single, picked colonies. However, in the context, 'isolate' can refer to a culture enriched for a bacterium or bacteria with desired properties, where the desired bacterial strain is at least 5% of the total viable cells, preferably 10%, 20%, 30%, 40%, 50%, 60%, 70%, 80%, 90% or 100%. The isolate or isolated microorganisms can be maintained as isolated and can be introduced into mixed cultures or contaminated cultures and used.

Lower alkyl alcohols: means $C_2$ to $C_5$ alcohols, i.e. ethanol, propanol, butanol, pentanol.

Neutral Detergent Fiber: means dry residue remaining after refluxing a feedstuff in pH 7 detergent for 1 hour in accordance with official procedures for fiber analysis, also called NDF.

Non-photosynthetic: means the organism does not use sunlight to produce complex organic compounds. Non-photosynthetic autotrophic organisms are chemotrophic and use chemical compounds (e.g. $CO_2$, $H_2$) to synthesize more complex chemical compounds (e.g. acids, alcohols, carbohydrates, proteins).

Mixed cultures: More than one isolate of microorganism cultured together, may be defined or undefined, pure or impure cultures.

Molar proportion: means the molar concentration of one product as a proportion of the molar concentration of all of a type of product. For example, the molar proportion of butyrate of 50% of all volatile fatty acids means that the number of moles per liter of butyrate is 50% of the total moles per liter of all volatile fatty acids.

Molar ratio: Means the molar concentration of one product over the molar concentration of another product. For example, a molar ratio of 1 for ethanol to acetate means the concentration of ethanol in moles per liter is equal to the concentration of acetate in moles per liter. The molar ratio of gases can also be determined based on the moles of gas per unit volume and pressure of the total gas.

Multi-carbon compound: means any compound with more than 1 carbon atom.

Organic: means a chemical element or compound in which one or more atoms of carbon are covalently linked to atoms of other elements, except for a few carbon compounds traditionally classified as inorganic including: carbon dioxide ($CO_2$), carbon monoxide (CO), carbides, carbonates (e.g. $HCO_3^-$), and cyanides.

Partial pressure of a gas: means the pressure a given species of gas. For example, if the total gas pressure is 1 atmosphere (atm) and carbon dioxide comprises 20% of the total gas by volume, the partial pressure of carbon dioxide would be 0.2 atm or 20% of the total gas pressure.

Plant fiber: Defined chemically as comprising cellulose, hemicellulose, pectin or lignin, or combination thereof, and found in plant cell wall and many forms of feedstock including whole plants, biofuel crops (e.g. switchgrass, algae), food byproducts, wood, wood byproducts, paper, waste, animal manure, human manure, and others.

Propanol tolerant: means that a microorganism is able to grow in the presence of propanol. Generally, this means an amount of propanol of at least 0.5 to 1% propanol by volume, and preferably about 2% propanol, even more preferably about 3%, 4%, 5%, or 6% by volume in aqueous media.

Pure cultures: Cultures of microorganisms that have been isolated or partially isolated to eliminate contaminant microorganisms. Cultures can be a single isolate or multiple isolates (mixed cultures).

Reducing conditions: means negative reducing potential (negative Eh) due to a high concentration of chemicals that donate electrons (e.g. $H_2$, CO, $S^{2-}$). Strongly reducing conditions have very negative Eh.

Rumen microorganisms: means any or all of the microorganisms found in the rumen of ruminant animals. This includes a diverse array of archaea, bacteria, protozoa, and fungi that digest fibrous plant material and ferment starches and sugars, for example. Many of these organisms also use metabolites transferred from other organisms such as sugars released by digestion, VFA exported from other organisms, or $H_2$ and $CO_2$. This term also includes such microorganisms that are also found elsewhere in addition to the rumen including the digestive tract of animals, feces, silages, sludge, or in soil among other places.

Single-carbon compound: means any compound with only one carbon atom. For example, carbon dioxide, carbon monoxide, bicarbonate, carbonate, formate, and methane.

Synthesis gases: means gases used to synthesize products. In the present invention the synthesis gases are usually carbon dioxide ($CO_2$), carbon monoxide (CO), and hydrogen gas ($H_2$).

Thermodynamically favorable: means the concentrations of reactants and products are such that the reaction is favored over other reactions.

Thermodynamically feasible: means the process can proceed spontaneously in the forward direction according to the second law of thermodynamics. In a thermodynamically feasible reaction, the multiplicative product of reaction product concentrations divided by the multiplicative product of reactant concentrations is low enough for the reaction to proceed spontaneously in the forward direction according to the calculation of the $\Delta G$ for the reaction. Observation of a reaction proceeding in the forward direction indicates that the reaction is feasible in consideration of all linked processes that enable the reaction to occur. In the present specification, thermodynamically feasible concentrations are calculated, wherein no alternative pathways are considered (e.g. ATP hydrolysis) unless otherwise stated, so the result shows whether an organisms can obtain energy from the conversion (i.e. $\Delta G<0$ indicates forward reaction releases Gibbs free energy).

Total gas pressure: means the gas pressure in the fermentation system including all gases whether added to the process or produced in the fermentation.

Undefined cultures: means cultures of microorganisms taken from a source without having isolated individual microbes or characterized individual organisms.

VFA: means volatile fatty acids (e.g. acetic acid, propionic acid, butyric acid, iso-butyric acid, valeric acid, isovaleric acid, succinic acid, and lactic acid). VFA concentration or volatile fatty acid concentration means moles or grams of acid and conjugate base forms all $C_2$-$C_5$ organic acids per liter or per 100 ml fermentation broth. For example, 5% VFA concentration means 5 g VFA per 100 ml.

Basis of the Invention

The present disclosure is based on U.S. Pat. No. 8,178,329 (issued May 15, 2012) and on U.S. patent application Ser. No. 13/381,127 (filed on Dec. 28, 2011), both of which are incorporated by reference in their entirely. In U.S. Pat. No. 8,178,329, isolated microorganisms and methods for their isolation and use were disclosed for fermentation of carbon dioxide or carbon monoxide to lower alkyl alcohols or organic acids. In U.S. patent application Ser. No. 13/381,127, isolated microorganisms, methods of isolation, and methods for production of alkanes were disclosed. In the present disclosure, additional microorganisms are described and additional processes are enabled including: compositions and processes with chemoautotrohic bacteria that use $CO_2$ or CO as a sole carbon source to produce an organic product. The organisms may be facultative aerobic. A process is enabled that uses microorganisms like these to produce lower alkyl alcohols or acids. A process is also enabled to specifically select for microorganisms of this type.

Chemotrophic organisms are able to obtain energy from chemical reactions of inorganic chemicals, such as iron, magnesium, sulfur, carbon monoxide, or hydrogen. Most known chemotrophic bacteria are chemoheterotrophic, which means they are unable to synthesize their own organic compounds from inorganic substrates (e.g. $CO_2$), and therefore they need to obtain organic compounds like carbohydrates, lipids, amino acids, or vitamins from their environment, although they can still obtain energy from catalyzing reactions of inorganic chemicals. Some organisms are chemoautotrophic, which means they are able to synthesize their own organic compounds from the fixation of carbon dioxide or carbon monoxide using the energy from inorganic molecules. Examples of chemoautotrophs include nitrogen-fixing bacteria in soil, and sulfur oxidizing bacteria in deep-sea vents. Most chemoautotrophic organisms take up and use organic material to complement their carbon dioxide fixation.

A basis of the present invention is the discovery by the inventor of chemoautotrophic microorganisms within the family Enterobacteriaceae that can grow by using carbon dioxide or carbon monoxide as the sole source of carbon. These organisms also produce and excrete multi-carbon compounds (e.g. acids, alcohols). Members of the Enterobacteriaceae family were discovered to grow readily from organic substrates, aerobically or anaerobically, but under highly reducing conditions they produce more of the organic substrates rather than degrade them.

Based on this discovery, the inventors realized that these bacteria could be incubated in fermentation medium under highly reducing conditions with CO or $CO_2$ as a carbon source, and the bacteria would synthesize organic compounds, including multi-carbon compounds like organic acids (e.g. $C_2$-$C_5$ carboxylic acids and alcohols). Thus, one embodiment of the present invention is to use a chemoautotrophic organism that can grow using single-carbon compounds, for example $CO_2$ or CO, as a sole source of carbon to produce organic products, preferably multi-carbon organic products. Another embodiment of the invention is to use Enterobacteriaceae bacteria in fermentations to convert inorganic or single-carbon compounds to multi-carbon organic compounds.

Microorganisms

The microorganisms isolated as one aspect of the present invention are capable of growth on $CO_2$ or CO as a sole carbon source, and many are aerobic microorganisms. Several isolated microorganisms were identified by 16S rRNA as being at least 97% identical to one of the genera: *Klebsiella, Citrobacter, Enterobacter, Salmonella,* or *Escherichia*, among others. Biochemical methods also confirmed that the organisms were aerobic and many strains grew on citrate as a sole carbon source under aerobic conditions. Growth on citrate as a sole carbon source is a common means of identifying members of the genera *Klebsiella* and *Citrobacter*. Some strains of *Escherichia* were confirmed not to grow on medium with citrate as the sole carbon source, but they grew on glucose under aerobic conditions. Thus, both biochemical and 16S rRNA methods confirmed the same identities. Motile strains included *Citrobacter* species.

Many of these genera are members of the family Enterobacteriaceae. The fact that different genera from the same family share the desired traits shows that certain desired characteristics of the Enterobacteriaceae are useful for the intended process to make organic products from single-carbon compounds. The Enterobacteriaceae are common bacteria generally found in the gut and other places. As a group, they are defined as being aerobic but oxidase negative (generally), and many species can survive on simple substrates (i.e. glucose or citrate). Many species are also tolerant to high variations in pH and are acid tolerant or alcohol tolerant. Most strains are harmless although some strains are pathogenic. Pathogenic strains can be readily identified, for example, by using polymerase chain reaction (PCR) with primers to amplify virulence or toxicity factors.

The organisms that comprise an aspect of the present invention were isolated for their traits including: 1) tolerance to lower alkyl alcohols, 2) ability to grow exclusively on $CO_2$ or CO, 3) ability to tolerate a high concentration of lower alkyl alcohol from the $CO_2$ or CO (e.g. at least 2, 3, 4, 5, 6% or more ethanol by volume). Known biochemical and physiological aspects of these facultative aerobic microorganisms include the ability to use the citric acid cycle pathway to convert acetic acid to citrate or intermediates, as well as the ability to oxidize organic acids to $CO_2$. However, observation that members of these species can use $CO_2$ or CO and $H_2$ or reducing agents to produce lower alkyl alcohols was surprising. Furthermore, the observation that some members of these species could grow while using a lower alkyl alcohol like ethanol as a sole carbon source was also surprising. The fact that some members were tolerant to the alcohols was also unexpected.

One aspect of the present invention is a microbial culture that can tolerate high concentrations of lower alkyl alcohols, such as at least 2%, 3%, 4%, or 5% ethanol by volume, and more preferably at least 6% or more ethanol by volume. Under highly reducing conditions, the isolated organisms grow in the presence of these high ethanol concentrations, and convert the gases $CO_2$, CO and $H_2$ to ethanol. Ethanol tolerant organisms also reflect tolerance to other lower alkyl alcohols. The same organisms also tolerate high concentrations of volatile fatty acids, such as 1%, 2% total volatile fatty acids by weight per volume or preferably 3% or more VFA by weight per volume (i.e. 10, 20, 30 g/L).

In addition, some isolated organisms can produce other products besides alcohols from synthesis gases. These products include acetate and longer-chain acids like propionate, and butyrate. The organisms tolerate high concentrations of the end products. Certain isolates specialize in producing alcohols like ethanol, while others primarily produce a certain VFA like butyrate from the synthesis gases. It is not necessarily advantageous to isolate or develop microorganisms that produce many different products. If many different products are produced, certain products may inhibit further fermentation, and it is more difficult to separate several products. Thus, one advantage of the isolated microorganisms that comprise an aspect of this invention is that many isolated strains specialize in producing few products. For example, they mostly produce alcohols or only short-chain volatile fatty acids (VFA) or mostly longer chain carboxylic acids. The inventors contemplate methods for isolating organisms that produce any particular set of carboxylic acids or alcohols for use in a specific process.

The present invention pertains to microorganisms that produce high concentrations of alcohols or desired carboxylic acids from gases, a combination of $CO_2$ and $H_2$, or CO and $H_2$, or CO, or a combination of all three gases. Some organisms that were isolated to use $CO_2$ and $H_2$ and produced a similar profile of products from CO and $H_2$. Others were isolated to particularly produce alcohols from CO.

Pathways for $CO_2$ or CO Fixation

There are few known pathways for microbial fixation of $CO_2$ or CO into more complex organic compounds. Organisms with all of these pathways would thrive in environments with high partial pressures of $H_2$ and $CO_2$ such as many anaerobic environments like an animal's gut, compost, beer fermentation, hydrothermal vents, or other anaerobic environments. By increasing the partial pressures of $H_2$ and $CO_2$, or CO, organisms with these pathways are favored and they can be isolated from the environment.

Some microorganisms use the Wood-Ljungdahl pathway, which uses a set of biochemical reactions to convert CO to acetyl-CoA by the enzymes CO-dehydrogenase and acetyl-CoA synthetase. The CO can be produced by many bacterial species from $CO_2$ and $H_2$.

Plants and some aerobic bacteria use the Calvin Cycle (a.k.a. Calvin-Benson-Bassham Cycle, or CCB Cycle, or Pentose Phosphate Cycle, or C3 Cycle). Some chemoautotrophic organisms can use the Calvin Cycle to reduce carbon dioxide with $H_2$ or sulfide to incorporate $CO_2$ into complex organic compounds. Many microorganisms from near hydrothermal vents were found to have the enzymes for the Calvin Cycle, and these include proteobacteria. The Enterobacteriaceae are members of the (gamma) proteobacteria and therefore may have enzymes for the Calvin cycle. Members of the Enterobacteriaceae include the gram-negative aerobic genera *Citrobacter, Klebsiella, Escherichia, Enterobacter, Salmonella, Serratia, Yersinia,* and *Proteus.*

Another means to fix $CO_2$ to produce more complex organic compounds is through the Reverse Krebs Cycle or Reverse Tricarboxylic Acid Cycle or Reverse TCA Cycle. The Reverse TCA Cycle is active in anaerobic microorganisms especially under high $H_2$ conditions. $CO_2$ is incorporated into $C_4$ and $C_5$ intermediates to produce citrate (a $C_6$ intermediate), which is cleaved to form acetyl-Co and oxaloacetate. Species of *Citrobacter* and *Klebsiella* can grow on medium with citrate as the only carbon source. This growth requires conversion of citrate to other all amino acid and carbohydrate precursors, and therefore the inventor reasons these species have the enzyme citrate lyase for cleavage of citrate to produce oxaloacetate and acetyl-Co, a key step in the Reverse TCA cycle.

Although some proteobacteria are known to have pathways for carbon dioxide fixation, including the Calvin cycle, the inventor was the first to discover certain species of proteobacteria, in the Enterobacteriaceae family, have a combination of traits: 1) they can fix carbon dioxide; 2) they can produce $C_2$-$C_5$ alcohols and carboxylic acids; 3) they can tolerate high concentrations of alcohols or acids, for example at least 2%, 3%, 4%, 5%, 6%, or more $C_2$-$C_5$ alcohols by volume or 1%, 2%, 3%, or more acetate or other VFA by weight per volume; 4) they are aerobic and can grow on several organic substrates including their own products from an anaerobic phase; and 5) they do not require complex nutrients like vitamins and organic substrates. The major genera of the Enterobacteriaceae include *Escherichia, Citrobacter* and *Klebsiella*, and representatives of each were found with the desired traits. One embodiment of the invention is to include a member of the Enterbacteriaceae or other chemoautotrophic bacterium in a fermentation to convert a single-carbon compound (e.g. CO or $CO_2$ and $H_2$) to an organic product (e.g. $C_2$-$C_5$ alcohols or acids). Preferably, the strain included would be selected through enrichment or isolation to be particularly tolerant to lower alkyl alcohols and/or organic acids. For example, strains enriched or isolated as an embodiment of the present invention can tolerate high concentration of acids and alcohols because of the way they were enriched for and isolated.

One aspect of the present invention is a process to isolate bacteria with all of these traits to use in production of organic chemicals. Isolated organisms that are especially suited for the production of lower alkyl alcohols or organic acids are another aspect of the invention. A process using organisms that can fix carbon dioxide by reduction with sulfide or $H_2$ or other chemical agent is described and enabled in the present specification.

Sources of Microorganisms

Many sources of microorganisms can be used to isolate facultative microorganisms for the present invention. Source may or may not include oxygen, because facultative organisms can survive anaerobic conditions. The original source of chemoautotrophic organisms was likely deep-sea vents, which released $CO_2$ and $H_2$ during the origin of life. The high underwater partial pressures of $CO_2$ and $H_2$ thermodynamically favor organisms that can convert the gases into more complex organic compounds. Similar organisms continue to thrive near deep-sea vents today, and they supply organic nutrients to higher life forms in the deep sea. These organisms are difficult to obtain, but similar chemoautotrophic organisms can also be isolated from many environmental sources on the surface of the earth.

Many of the organisms used in the present case were taken from the rumen (stomach) of a cow. The rumen is consistently warm favoring rapid metabolism and hosting more than $10^{10}$ organisms per ml. The rumen gas phase is largely comprised of carbon dioxide and methane with enough hydrogen to make it thermodynamically feasible to produce carboxylic acids. Rumen microbes produce several liters of $H_2$ per day and much more $CO_2$ and these gases are transferred among microbial species and incorporated into CO, formate, methane and carboxylic acids. The mixed culture rumen microorganisms are well known to produce acetic acid from $CO_2$ and $H_2$, and these microbes also convert acetic acid to other volatile fatty acids by incorporating $CO_2$ and $H_2$ to produce propionic acid, butyric acid, and longer chain acids. Rumen microbes are also well known for production of ethanol although ethanol does not accumulate in the rumen because it is subsequently converted to other products. Microbes may be removed from the rumen of a cow by taking them directly from a fistula inserted into the cow's side. Additionally, microbes can be obtained using a stomach tube, or they may be obtained from a slaughterhouse. Microbes may be taken from the feces of a ruminant or from the hindgut as well.

There are many other sources of microorganisms that can be used in place of microorganisms from the rumen of a cow. For example, microbes may be taken from the gut or feces of any other ruminant such as deer, antelope, bison, or camel. They may also be taken from elsewhere in a digestive tract of any type of animal including mammals or non-mammals. Even insects like carpenter ants or carpenter bees or termites host large numbers of microbes that may be suitable. Microbes may be obtained from soils, water bodies, compost, or manure digesters. Fermented foods may also host suitable organisms. For example, wine, cider and beer host organisms that are tolerant to acids and ethanol and that may use and/or produce ethanol. The organisms in the ruminants gut are inoculated from environmental sources over the course of the animal's life as the animal is born devoid of most organisms. Thus, many different environmental sources can be used to obtain organisms, although the ruminant improves and enriches the organisms in the environment to suit its needs.

The following functions can be orchestrated by microbial cultures obtained from a mixed culture such as exist in the rumen of the cow and many other natural and diverse ecosystems. These are functions that may not be observed under natural conditions because of the need to limit some activity that would naturally be present. For example, the production of biofuels or other desired products from synthesis gases, as opposed to production of acetic acid, is as much about limiting enzyme activity as it is about adding it. Isolation of microorganisms can often be used to limit the activity in the system because in nature the metabolites are passed from one organism to the others, thus not providing organisms to pick up the metabolite can enable a desired metabolite's accumulation. This application focuses on the way to effect the following activities using microbial cultures, as well as ways to develop the microbial cultures themselves:

a. Conversion of $CO_2$ and $H_2$ to acetic acid. The acetic acid can be further converted to other acids or alcohols with the same or other cultures.
b. Conversion of $CO_2$ or CO and $H_2$ to alcohols. The inventors discovered and isolated organisms from the rumen of a cow that convert $CO_2$, CO and $H_2$ to $C_2$-$C_5$ lower alkyl alcohols.
c. The interconversion of acids and alcohols. The direction of interconversion would be controlled by thermodynamics.
d. Conversion of carbon monoxide (CO), to acetic acid. This process is a means to use gases produced from high-temperature physical digestion. The process can use the same pathway for the conversion of $CO_2$+$H_2$→acetyl CoA by starting on a second step. Wherein $CO+H_2O \leftarrow\rightarrow CO_2+H_2$ is a rapid process at moderate temperature, the system that assimilates $CO_2$ and $H_2$ into longer carbon chains also assimilates CO and $H_2$. The inventors discovered that most of the organisms that produce volatile fatty acids or lower alkyl alcohols from $CO_2$ and $H_2$ produce a similar profile of end products from CO and $H_2$.
e. Conversion of CO and $H_2$ to ethanol. Several organisms were isolated from the rumen that could carry out this process.
f. Conversion of organic acid to alkyl alcohol. For example, lactic acid conversion to ethanol, or butyric acid conversion to butanol.
g. Conversion of one organic acid to another. For example, acetic acid converted to propionic acid, or acetic acids converted to butyric acids, or further elongation of carboxylic acids, or shortening of carboxylic acids.
h. Conversion of acetic acid to $H_2$ and $CO_2$, which could also include acetic acid degrading organisms. These organisms would be used in combination with a way to make acetic acid degradation thermodynamically favorable such as by purging of gases.

Often more than one function above would be combined. For example, one microorganism may use $CO_2$ and $H_2$ to produce acetate (function a), while another one may convert the acetate to ethanol or butanol (function c). This combination could result in production of longer-chain alcohols from $CO_2$, CO and $H_2$.

Desired Characteristics of Microorganisms to Assimilate Synthesis Gases

An aspect of the present invention is the means to obtain pure cultures of microorganisms that can tolerate high concentrations of alkyl alcohols and acids while they produce additional alcohols or acids.

The present application describes the means to enrich for or select microorganisms that can be used to produce products synthesized from gases. The first step to synthesize or enrich for these organisms is to identify the desired physiological traits for the organisms. Understanding these desired traits enables the establishment of conditions where the organisms with those traits thrive The ideal characteristics of desired organisms are as follows:
  Produce desired product or products from gases (CO, $CO_2$, $H_2$)
  Produce desired product or products nearly exclusively
  Produce desired product or products to a high concentration
  Produce desired product or products at a high rate At some concentration of product, such as ethanol or acid, the microorganism that produces the product is in deed intolerant to the further concentration of the product even after adjusting for the other product and reactant concentrations. For example, enzymes or cell membranes may be inhibited by the product. Another aspect of the present invention includes isolation and identification of microorganisms that are tolerant to high concentrations of the desired products: ethanol, propanol, butanol, acetic acid, propionic acid, or butyric acid, other alcohol or acid, or a combination thereof. The process to isolate the microorganisms themselves with high tolerance to their products, and the methods to isolate them are both aspects of the invention.

The organisms that comprise an aspect of the present invention are also able to produce the desired products at high rates. The organisms are isolated and screened for such high rates as an aspect of the present invention.

Other characteristics of the microorganisms that may be desired but not required include characteristics that make them easier to handle or more versatile including:
  Ability to tolerate or use oxygen
  Ability to digest biomass including cellulosic biomass
  Ability to grow the organisms on undesired co-products they produce during carbon fixation.

The inventors isolated microorganisms that can assimilate $CO_2$, CO and $H_2$ into ethanol while the concentration of ethanol exceeds varying concentrations ranging form 0%, 1%, 2%, 3%, 4%, 5%, 6%, 7%, 8%, 9%, or 10% by volume. The thermodynamic analysis showed that it is feasible to produce high concentrations of ethanol from high $CO_2$, CO and $H_2$ concentrations. At low pressures of these gases, or if the ratio is skewed against the carbon or hydrogen side, it is thermodynamically more favorable to degrade ethanol than to produce it. However, by increasing the partial pressures of CO, or $CO_2$ and $H_2$, it becomes thermodynamically feasible to produce lower alkyl alcohols and organic acids rather than degrade them. In fact, the very products that are made from $CO_2$ and $H_2$ can be degraded to provide energy for microbial growth when $CO_2$ and $H_2$ concentrations are low, or under aerobic conditions.

Methods of Microbial Enrichment and Isolation

One approach to obtain organisms that carry out a desired conversion reaction (e.g. A→B) is to isolate organisms that carry out the reverse of the desired pathway (e.g. B→A). In other words, one can enrich them under conditions that start with a high concentration of the desired product and favor degradation of the product. In a subsequent enrichment phase, the desired product is removed and the thermodynamic conditions are reversed. The resulting organisms can create the desired product under one set of conditions and degrade it under another set. This approach applied to enrichment of organisms selects for a high degree of tolerance to the desired product (only organisms that grow in a high concentration survive) and a high specificity of production (selected organisms have the enzymes to make or degrade the desired product). It is based on the theory that all catalysts decrease activation energy of reactions, and they do not change the equilibrium constant or ΔG. Catalysts such as enzymes accelerate the rate of reactions when those reactions are kinetically controlled, but they must also accelerate the rate of the reverse reactions to an equal proportion. Otherwise the equilibrium constant would change. A corollary to this principle is that all catalyzed reactions are bi-directional. If we seek enzymes to catalyze a given reaction, for example to produce butanol, organisms that degrade butanol have those enzymes. The cell machinery may not be set up to allow the organisms to grow (produce ATP) under both sets of conditions, but many organisms can obtain energy by metabolizing the reaction in either direction.

Aerobic conditions were used during enrichment of microorganisms in a preferred embodiment of the invention. Many organisms can aerobically catabolize a substrate like glucose, citrate, or alcohol to $CO_2$ and $H_2O$. However, they may also survive under anaerobic conditions by making another end product that does not require oxidation. For example, they may make acetate and $H_2$ or ethanol or lactate. If oxygen is returned to the environment, they may further oxidize these "end products" to $CO_2$ and $H_2O$ for additional energy. Thus, it is advantageous to isolate such facultative aerobes by growing them in the presence of oxygen and high concentrations of the desired product. For example, the inventors used this technique for isolation of facultative aerobes that produced alcohols from $H_2$ and $CO_2$. In one phase of the enrichment, the alcohol was oxidized to $CO_2$ and $H_2O$, and in the other phase, organisms were grown under conditions to favor production of the desired acid from $H_2$ and $CO_2$. There are special advantages of facultative aerobes. They can be grown aerobically very quickly while only producing $CO_2$ and $H_2O$, which can be easily removed. In a preferred embodiment, medium comprised minerals but no carbon sources other than the desired product (e.g. ethanol, 1-propanol, iso-butanol, 1-butanol). Concentrations of the alcohols are varied (e.g. concentration may be 0.5%, 1%, 2%, 3%, 4%, 5%, or 6% total lower alkyl alcohol by volume, or even as high as 7%, 8%, 9%, 10%, or higher lower alkyl alcohol by volume. The higher concentrations select for more alcohol tolerant microorganisms, but as the concentration is higher fewer strains can survive, limiting options to find other desired traits such as high growth rates.

One embodiment of the invention is enriching or isolating microorganisms by growing them under aerobic conditions consuming what will be the eventual desired product as substrate, wherein the eventual desired product is included at a high enough concentration to select for aerobic organisms tolerant to high concentrations of the desired product. The concentrations of the substrates can be varied. For example, the inventors used several alcohols and acids at many different concentrations. The higher the concentration, the fewer strains continue to survive, but the resultant isolates can tolerate those high concentrations. However, at slightly lower concentrations, more robust or rapidly growing organisms can be isolated. Therefore, the inventors used several different concentrations for comparison. The concentrations of ethanol for different enrichments may be 0%, 0.5%, 1%, 2%, 3%, 4%, 5%, 6%, and as much as 10% (v/v). The inventor discovered that organisms could survive and grow in enrichments of more than 10%. The concentrations for other alkyl alcohols may also be varied, for example 0%, 0.5%, 1%, 2%, 3%, 4%, 5%, or 6% (v/v) $C_3$-$C_5$ lower alkyl alcohol can be used by adding the specific alcohol to the enrichment. The inventor found that organisms from the rumen of a cow grew in enrichments with up to 6% 1-propanol or 1-butanol. The concentration of organic acids can also be varied, such as 0%, 1%, 2%, 3%, 4%, 5%, or 6% (w/v). The inventors discovered that organisms from a mixed culture from the rumen of a cow grew in concentrations of acetate greater than 5.4%, and degraded acetate to gas when incubated in $CO_2$ environment, or produced more acetic acid and used gas when incubated with 4 atm pressure of $H_2$ and $CO_2$ gas at a ratio of 3:1. Thus, the enrichment process shows that organisms exist the are extremely tolerant to the desired products and that can degrade or produce the products depending on the conditions of pressure and composition of the medium.

Once the aerobic microorganisms that can degrade the desired products such as ethanol or a butanol are selected for under aerobic conditions, individual isolates that can use carbon dioxide or carbon monoxide as a carbon source are selected from the previous culture. Alternatively, bicarbonate ($HCO_3^-$) may be the carbon source. Bicarbonate is in equilibrium with carbon dioxide in liquid medium as the two are readily interconverted and microorganisms may use either form. In this step, the culture of microorganisms enriched in the previous step is incubated in a medium under conditions with high pressures of carbon dioxide and hydrogen or carbon monoxide or other reducing agent. Reducing agents may also include sulfide or reduced metals or organic chemicals like formate. The enriched culture may be diluted serially or a streak plate may be used. The objective is to isolate single cells that reproduce under favorable conditions to form individual colonies that can be selected. The colonies can be "picked" or transferred to sterile broth and grown under conditions thermodynamically favoring the desired products and tested for production of those products.

Alternatively, the enrichment can be under conditions selecting for growth on $CO_2$ or CO, and selection can be under similar conditions or even aerobic conditions. The steps can also be taken in the opposite order, or repeated enrichment steps can also be used and alternated.

This enrichment process discovered organisms identified as belonging to a genera such as *Citrobacter* or *Klebsiella*, some isolations were undertaken by streaking or inoculating dilute cultures to agar plates containing citrate as the sole available carbon source under aerobic conditions. Under these conditions, *Citrobacter* and *Klebsiella* can grow readily. *Citrobacter* and *Klebsiella* microorganisms are known for aerobic growth on citrate as a sole carbon source. Many were found to be tolerant to more than 6% ethanol by volume. Members of these genera are known to have an active citric acid cycle pathway, and many steps in the pathway can be reversed. As aerobic microorganisms, they may alternatively or additionally have enzymes from the Calvin Cycle pathway. Either the reverse citric acid cycle or Calvin cycle would enable conversion of the gases, under moderately high partial pressures, to be converted to alcohols or acids, and Gibbs free energy would be released or made available to be used by the microorganisms to support growth.

The microorganisms that can be isolated to assimilate alcohols and VFA from synthesis gases (e.g. $CO_2$, CO, $H_2$) and that would be tolerant to the products they produce, are disclosed as an aspect of this invention. These microorganisms continue producing the products even when the concentration is high. The way to manipulate other metabolites to make the high concentrations thermodynamically favorable, and undesired products unfeasible has been disclosed as an aspect of a previous invention by one of the same inventors (U.S. Pat. No. 8,178,329), which is incorporated in its entirety by reference. Using conditions of moderately high partial pressures of gases (to be described) to enrich, select and isolate microorganisms that can produce desired products at high concentrations is another aspect of the invention. For example, microorganisms can be isolated in the presence of high concentrations of 1-butanol or 1-propanol (e.g. more than 0.5% alcohol by volume, or more preferably at least 1%, 2%, 3%, 4%, 5%, 6%, or more than 6% total lower alkyl alcohol or predominantly one lower alkyl alcohol), and with thermodynamic conditions to synthesize these alcohols from gases (e.g. high partial pressures of the gases at a ratio of 3 to 1 of $H_2$ to $CO_2$). It is thermodynamically feasible to make more of the alcohols even at high concentrations so organisms that carry out the reaction are favored. Alternatively, for a step in the process, microorganisms that utilize the alcohols can be selected by incubating in high concentrations of the respective alcohol under aerobic conditions that favor degradation of the alcohol. In a subsequent step, these microorganisms can be selected under high $CO_2$ and $H_2$ or high CO and $H_2$ at optimal ratios so that the organisms that can obtain energy from the opposite pathway are selected.

In general, the unique aspects of the microbial isolation methods for microorganisms that are especially suited for synthesis of alcohols or acids from synthesis gases that are an aspect of the present invention are as follows:

Isolation with high concentrations of the desired product (e.g. any lower alkyl alcohol or organic acid, or a combination of more than one)

Isolation under conditions that thermodynamically favor the product formation (calculations can be performed to insure $\Delta G$ is negative or strongly negative for production of the desired product from CO, or $CO_2$ and $H_2$, at the partial pressures of the gases.)

Where the $\Delta G$ is strongly negative, growth rates of organisms that produce the desired products will be faster. Furthermore, in the present application, isolation often utilized an aerobic step and an anaerobic step to obtain facultative aerobic microorganisms that could be used to produce alcohols or acids. However, the inventor also isolated organisms under conditions of $CO_2$ or $N_2$ pressure wherein it was thermodynamically feasible to degrade an organic product anaerobically.

For example, ethanol-tolerant microorganisms that produce ethanol from synthesis gases were selected by growing a mixed culture for many generations in the presence of the gas concentrations that favor ethanol producers more than acetic acid producers. These conditions include high $H_2$ partial pressures. Acetic acid was further inhibited in some cases by growing the cultures at pH less than 5. After enrichment, the culture was diluted to isolate individual colonies that grow from gases as the only energy source (in a ratio favoring ethanol, 3:1 of $H_2$ to $CO_2$), and which may include ethanol in the media. With a different gas mixture, ethanol would be degraded but calculations showed that it would be thermodynamically infeasible to degrade it, even at high ethanol concentrations, at high partial pressures and the ratio of 3:1 of $H_2:CO_2$. The same process can be applied to carboxylic acids and other products. The total pressure of gases may be about 1 atm, or at least 2, or 3 atm., or preferably 4 atm.

The enriched and isolated microbial compositions that comprise an aspect of the present invention differ from previous isolates because they were selected and developed specifically for the combination of traits desired for the process to produce alcohols or acids. Although many members of the species isolated as a part of the present invention have been isolated previously and were determined to be aerobic, non-fastidious, and to grow on simple media, other desired attributes were not selected for or screened. The isolates that comprise an aspect of the present invention were selected for high tolerance to acids and alcohols, and tolerance to other products could also be selected for, and the ability to use CO or $CO_2$ and $H_2$. These attributes have not been determined for most members of the Enterobacteriaceae, and certainly have not been enriched or selected for. When the inventors set out to isolate the microorganism, no one knew which species if any would grow on weak media with no organic carbon under high $H_2$ pressure. Of the stains that could grow on the weak media, no one knew which strains would be most tolerant to alcohols or acids, and harbor all of the desired traits. Nor did anyone know how tolerant the organisms could be to the alcohols and acids. Thus, the isolates described in the present invention are novel and non-obvious.

Example Process to Isolate Microorganisms that Synthesize Alcohols and Acids from Gases Several different sets of conditions were used to select for aerobic microorganisms that could produce alcohols or acids from $CO_2$, CO and $H_2$. In one approach, conditions that result in degradation of the desired alcohols select for organisms that can also synthesize the desired alcohols or acids. Thus, in some cases conditions were established to enrich or isolate the degraders of products rather than the producers of the products directly. This enabled more specific selection of organisms that were tolerant to a certain product and which had the pathway to make the certain product. For example, microorganisms that degraded 1-butanol to $CO_2$ and $H_2$ also had the enzymes to make 1-butanol from $CO_2$ and $H_2$. On the other hand, an organism that uses $CO_2$ and $H_2$ could make many different products including other alcohols and acids and may not be ethanol tolerant.

Aerobic or aerotolerant microorganisms were selected. These were easier to handle in some applications. After enrichment by growing the cultures with the desired alcohol in air, organisms that could grow on CO, or $CO_2$ and $H_2$ were enriched, selected and isolated. These organisms produced a number of different products, which were determined through analysis on a gas chromatograph or other procedure. Using a ratio of $H_2:CO_2$ of 3:1, pressure of 2 to 4 atm and alternatively moderately low pH (e.g. 4-5) favors alcohols over acids. This combination of conditions can be used to shift fermentation toward alcohols. Previous investigators did not isolate organisms under conditions that made the desired alcohol or carboxylic acid thermodynamically feasible, and especially not thermodynamically favorable compared to other potential products.

For example, the ratio of $H_2$ to $CO_2$ could be higher, such as 10 to 1 or 100 to 1 while it is still feasible to produce some ethanol rather than degrade it. This higher ratio shifts fermentation further in favor of alcohols or longer-chain carboxylic acids over acetic acid, and conditions can be established in which it is only feasible to make ethanol and not make acids. Many of these enrichments were undertaken with 2 to 4 atm total pressure to further shift the fermentation toward alcohols and longer-chain acids. In some cases, the enrichment or isolation pressures were as much as 8 atm. Chambers were made from steel pipes to conduct the fermentation at high pressures. It is also advantageous to include alcohols in the enrichment or in the isolation medium and when the ratio of $H_2$ to $CO_2$ or $H_2$ to CO is near the optimal level, and especially when under greater than 2 atm and preferably greater than 4 atm total pressure. It is still thermodynamically feasible to produce more of the alcohol or desired acid. This inclusion increases selection pressure to obtain more alcohol-tolerant organisms. It is also advantageous to include acetic acid or other VFA in the media during enrichment or isolation as the VFA inclusion shifts equilibrium against further VFA production and also selects for organisms that are tolerant to higher concentrations of VFA. Individual VFA or a mixture of several VFA were used. Some organisms may be intolerant to the VFA and would be selected against, while others can grow in the presence of VFA. These isolations were conducted at pH 7 or pH 5 with or without 3% mixed VFA. Isolates were also obtained at pH 4, and higher or lower pH could also be used.

The lower pH and the aerobic conditions selected for organisms that produced greater molar ratios of ethanol to acetic acid even when incubated at pH 7 under similar conditions following the isolation.

Medium for enrichment, isolation, screening and initial experiments was as described for in vitro digestion according to the manual by H. K. Goering and P. J. Van Soest, 1970. (Agricultural Handbook No. 379 entitled Forage Fiber Analyses (Apparatus, Reagents, Procedures, and Some Applications, Agricultural Research Service of the United States Department of Agriculture), which is incorporated by reference. When low $CO_2$ medium is desired for growth of microorganisms under CO pressure, carbonate and bicarbonate salts (e.g. $NaHCO_3$, $NH_4HCO_3$) were replaced with equi-molar phosphate buffer salts (e.g. $NaH_2PO_4$, $NH_4H_2PO_4$) adjusted to pH 7 or pH 5 unless otherwise indicated. Macro minerals (e.g. calcium, magnesium), microminerals (e.g. iron), ammonia, sulfide and cysteine reducing agents, and resazurin were used as described by Goering and Van Soest (as cited). Tryptic digest of casein was omitted in the present embodiment to select for microorganisms that can grow without any organic carbon sources. When media contained some amount of carbon skeletons (i.e. amino acids, yeast extract), several species of *Enterococcus* or *Clostridium* were isolated that produced high concentrations of ethanol or acids. These cultures can be used with the added ingredients or in co-cultures with the less fastidious microorganisms isolated without organic carbon. Media were boiled under 1 atm $N_2$ gas or $CO_2$ (for cultures with CO2). The same media formulae were used for initial enrichment, agar roll tubes, broths, slant tubes, and agar plates. However, roll tubes, slant tubes and agar plates also contained 2% agar (BACTOAGAR®).

Enrichment. Media minimized extraneous sources of energy (e.g. glucose, amino acids, vitamins), to select for organisms that could grow from the energy they captured from the gases or from the included alcohol or acid. Medium (45 ml) was transferred to each flask. Rumen fluid was collected from the cow's rumen through a fistula and was initially prepared by blending for 1 minute and straining though cheese cloth followed by glass wool. Initially, most enrichments were conducted anaerobically, but when using weak media that did not contain carbon sources, even under anaerobic conditions, facultative aerobes were isolated. Therefore, subsequently aerobic conditions were used in some stages of enrichment. For anaerobic states, carbon dioxide, run through a copper column to remove $O_2$, was perfused over rumen contents and into containers to maintain anaerobic conditions. Rumen inocula (5 ml) was added to each 250-ml flask. Large flasks relative to the volume of liquid were used so the headspace composition of gases did not readily change. Flasks were sealed with butyl rubber stoppers, and if needed vacuum was applied to remove initial head space gas before perfusion with corresponding treatment gases using a needle and syringe. Cultures were incubated in a shaking water bath for 3 days, and new gases were perfused at least daily. New flasks were prepared with 45 ml of media, and 5 ml of subculture was added from the previous fermentation. These flasks were again incubated for 3 days, and again sub-sampled. Each enrichment process included several cycles of sub-culturing and growth. Many variations on enrichment culture conditions are acceptable or advantageous, and can be applied. For example, often cycles were longer than 3 days and as long as 14 days in the present experiments, as many non-fastidious organisms grow very slowly under anaerobic conditions.

For each enrichment and roll tube, the temperature of incubation was 39° C. unless indicated otherwise. Organisms were also selected at 55° C. and other temperatures could have been used. Using different temperatures selects for organisms that thrive at different temperatures. Initially, various concentrations of alcohols or acids were used. These conditions selected for organisms that could utilize the alcohols or acids, and which therefore also had the enzymes to make the alcohols. The same can be done for specific carboxylic acids. Each enrichment and isolation was attempted with media buffered to pH 7, pH 5, or pH 4. The lower pH favored alcohol producers and the isolates that resulted produced a greater concentration of ethanol and other alcohols relative to acetic acids and other volatile fatty acid production.

In some cases, the enrichment can include phases under reducing conditions, and moderately high pressures of CO, or $H_2$ and $CO_2$. For example, enrichments may include CO or a 3:1 ratio of $H_2$ to $CO_2$ at 4 atm pressure. These phases may use weak media with no carbon source other than dissolved CO or $CO_2$, and the readily formed intermediates (e.g. $HCO_3^-$ or formate), and an inorganic source of nitrogen like ammonia. Alternatively, these phases can include the desired product, like ethanol, butanol or an organic acid at a concentration to continue selecting for tolerance to the products. Since the gas composition and pressure makes in thermodynamically infeasible to degrade the products to $CO_2$ and $H_2$, organisms that can grow by making more desired product are still selected.

Isolation. Agar plates used the same medium as for enrichment except included BACTOAGAR®. The prepared medium was transferred to sterile plates while still hot from autoclaving. Subcultures from the last enrichment were diluted serially in media to obtain cultures from 1 to $10^{-14}$ viable cells per 0.5-ml inocula. Plates were inoculated for each level of dilution. Once inoculated, plates were placed in pressure cookers, which were perfused with gas. After applying vacuum and refilling 4 times with $CO_2$, pressure in the pressure cooker was decreased to 0.5 atm, and then filled to 2 atm with $H_2$ (final result 3:1 $H_2$:$CO_2$, 2 atm). Alternatively, higher pressures were used in steel pipes, and 2 atm CO was also used. Samples were incubated for 24 to 48 h at 39° C. and independent colonies selected from these. Only organisms that could grow using the gases as an energy source were selected in the roll tubes. Some plates were buffered to pH 4, 5 or 7 and sometimes VFA or alcohols were included in the plate medium.

Maintenance. Colonies were selected from among the colonies in roll tubes and agar plates, and were transferred to broth for short-term maintenance. The broth was of the same composition as media for other purposes, but did not contain agar. All cultures were maintained in large tubes leaving a high proportion of headspace, the ratio of $CO_2$ to $H_2$ or CO to $H_2$ that favors synthesis of the alcohols, and gas pressures of 2 atm to 4 atm. Broth cultures were maintained at 39° C. until they become cloudy, and new gas mixes were perfused if necessary. Broth cultures (5% final concentration, vol/vol) were transferred to new media one to two times per week. After two to three cultures, 0.1 ml culture was transferred to a slant culture in a 25-ml tube with 10 ml media on a slant to increase surface area). The inocula was added on top of the agar, which was maintained under $CO_2$ and $H_2$ or CO and $H_2$ in the thermodynamically favored ratio. These were initially incubated at 39° C. until colonies formed (16 h), and then stored at 25° C. or 4° C. for up to a month. Cloudy broth cultures were also stored by adding 15% glycerol (final volume) and freezing in liquid nitrogen; once frozen, these colonies were stored at −80° C.

Screening. Screening of microorganisms addresses whether they can synthesize a certain alcohol or acid from $CO_2$, CO, and $H_2$, and the extent to which they are tolerant to the product. The isolates derived as described were screened by transferring 0.5 ml broth to 9.5 ml media (as described, no agar). Tubes were perfused with mixtures of $CO_2$, CO and $H_2$ to favor synthesis (e.g. 3:1 ratio of $H_2$:$CO_2$) of the desired product preferably under at least 2 atm total gas pressure. Preferably 4 atm total gas pressures are used. However, successful isolations were also performed with only 1 atm total gas pressure with the ideal ratio of gases. The pH of the media was adjusted to 7, 5, or 4 and 3% or 6% mixed VFA added for different runs. Many other concentrations or combinations can also be used. Samples were also incubated with and without initially including 6% or other concentration of an alkyl alcohol in the media. The cell growth was determined by turbidity, and alcohols and acids were measured by gas chromatograph at time=0, and other time points (e.g. 3 d and 5 d). All colonies were typically screened after first isolating them by adding the colony directly to a test tube with media, incubating with $H_2$ and $CO_2$ and determining which isolates produce the highest concentrations of desired products or show other desired traits. The isolates that appeared to be most ideal were sub-cultured and incubated again in fresh media in replicate to verify results and test for effect of different conditions (e.g. pH, gas pressure) of the fermentation.

Improving Organisms that Synthesize Alcohols or Acids

These same conditions to enrich or isolate microorganisms that produce high concentrations of alkyl alcohols or acids from $CO_2$, CO and $H_2$ were used to improve the isolated microorganisms. Some improvements occur in the enrichment or isolation process although the improvements may not be observed. Pure cultures of microorganisms can be incubated with the ratio and pressure of gases that thermodynamically favors synthesis of the desired alcohol or acid, under pressures (e.g. 2 to 4 atm or higher), and in the presence of the products to which tolerance is desired. Under these conditions, organisms that produce the most of the desired product thrive, while those that produce more of the undesired product waste energy and become diluted. Over many generations, which can occur in a matter of days, organisms evolve under these conditions that can synthesize greater quantities of the desired product relative to other products, at faster rates, and that are more tolerant of the product and potential co-products. Mutation rate can be increased by brief exposure to UV light or other mutagen combined with thermodynamic controls. Using these conditions and several subcultures for enrichment of pure cultures, organisms can be developed that make only the desired products, at high rates, with high tolerance to those products. This process of directing evolution (or non-specific mutagenesis) selects for organisms on the basis of the products they make, and selects for organisms that can tolerate very high concentrations of products.

Previous attempts at non-specific mutagenesis did not select for organisms that produced specific products, so one could not increase the amount of those products produced as a portion of total products. As a result, many different products were made. In addition, previous methods at adaptation to higher levels of products (e.g. alcohols) by growing the isolates with the products selected against further production of those products (because they became thermodynamically limited). By maintaining highly thermodynamically favorable conditions for the production of desired products (e.g. alcohols) organisms are adapted that produce the desired products even at high concentrations. Using this process, the inventors contemplate isolating organisms that can produce a desired alcohol or desired carboxylic acid nearly exclusively, and at very high concentration.

Process to Produce Alcohols or Acids

One embodiment of the invention is to improve processes to produce lower alkyl alcohol from CO or $CO_2$ and $H_2$ by adding the isolated or similar microorganisms. Aerobic microorganisms such as members of the Enterobacteriaceae family including members of the genera *Citrobacter, Klebsiella, Escherichia, Enterobacter*, and *Salmonella* can be added to the fermentation to support the growth or survival of strict anaerobic species like members of the genus *Clostridium*. The aerobic organisms can use oxygen and make the fermentation more stable. These organisms can also provide complex organic nutrients, e.g. amino acids, to the more fastidious species. The present disclosure enables isolation and development of alcohol and acid tolerant strains that are an aspect of the invention. Including these aerobic microorganisms that are tolerant to the desired products in the fermentation broth enables them to survive and contribute to improve the overall fermentation even if it is, in part, orchestrated by another organism. Preferably, the alcohol and acid tolerant microorganisms also make the desired products from single carbon compounds under reducing conditions.

Most of the aerobic isolates that can grow using only carbon dioxide or carbon monoxide as a carbon source grew slowly under anaerobic conditions from syngas. For example, the isolates that grew from syngas in media with yeast extract (e.g. gram positive species such as *Enterococcus*) produced colonies from single cells in only 16 hours. In contrast, colonies were initially produced only after five to ten days for the isolated non-fastidious aerobic organisms (e.g. gram negative) when grown on $H_2$ and $CO_2$ gases in media with no organic compounds. However, the latter non-fastidious organisms formed colonies within 16 hours when using glucose, citrate or an alcohol or acid as the substrate under aerobic or anaerobic conditions. Therefore, a process to produce chemicals from CO, or $CO_2$ and $H_2$ may involve a first step in which the aerobic microorganisms are grown in medium with an organic substrate, then the container is closed to allow the conditions to become anaerobic. This population can be infused with 2 to 4 atmospheres of CO, or $H_2$ and $CO_2$. Under these conditions, the organisms can produce alcohol or acid at a rapid rate to a high concentration such as producing ethanol to 5%, 6%, 7%, or 8%, or higher concentration by volume. The broth can be diluted or filtered or centrifuged to recycle the bacteria. Alternatively, a portion of the alcohol can be distilled using vacuum pressure to preserve the microorganisms. The broth containing other organic products can be returned to the digester and additional alcohol produced. The more fastidious organisms such as *Enterococcus avium*, or *E. casselflavus, E. durans*, or *E. feaceum, E fecaelis*, or *Clostridium*, among others can also be included in the fermentation as the inventors isolated strains of these species, which also produce ethanol or other alcohols or products to a high concentration using CO, or $CO_2$ and $H_2$. When using strict anaerobes, the oxygen is scavenged by the aerobes, and the fastidious organisms can obtain nutrients produced by the non-fastidious organisms.

The invented process to produce lower alkyl alcohols or organic acids may comprise different steps: a biomass-degrading step, which may be aerobic, can support growth of the desired organisms, and a reducing step in which the microorganisms convert the $CO_2$ or CO to the desired lower alkyl alcohol or acid. It is well known that the growth of any organisms that converts CO or $CO_2$ and $H_2$ to organic products is very slow, and so obtaining organisms that can alternatively grow from undesired products is desired. This biomass-degrading step can also be anaerobic, but as long as biomass is provided, it can be used to support microbial growth of the organisms that use $CO_2$ and CO. Therefore, it is desired to obtain organisms that can grow by degrading biomass and subsequently can also use CO or $CO_2$ and $H_2$ to produce desired acids or alcohols. The biomass could be glucose, citrate, alcohols, acids, cellobiose or plant fiber (e.g. ligno-cellulose, hemicellulose), manure, crop residue, brewery waste, or many other forms. The inventors isolated several organisms that can both degrade various forms of biomass and use CO or $CO_2$ and $H_2$ to produce desired products under reducing conditions.

Once the microbial population is established, reducing agents and additional $CO_2$ may be added to the fermentation. Alternatively, $CO_2$ from the biomass-degrading step can be recycled. Reducing agents may include $H_2$, $H_2S$, electrons from an electrode, reduced metals, CO, or formate. In addition, a simple carbon source such as $CO_2$, $HCO_3^-$, CO, or formate may be supplied. In the reducing step, fermentation of $CO_2$, $HCO_3^-$, CO, or formate under reducing conditions causes the microorganisms to produce the desired products. The gas from one stage may be pressurized to make it thermodynamically feasible to produce the desired products from the gas fermentation. The desired products may be removed after the reducing step, and the microorganisms and the other products and liquids returned to the biomass-degrading step in which the microorganisms may be rapidly grown. The co-products from the reducing step, which may not be as desired, may provide organic substrate for growth of additional organisms, and production of additional desired product and $CO_2$.

The steps may occur at the same time, or may occur in sequence, in the same reactor under different conditions, or in different reactors. For example, one strain of microorganism in the same vessel may degrade biomass while another strain uses excess $CO_2$ and $H_2$ that is released. It may even be the same microorganism that both degrades biomass and reduces released $CO_2$. The vessel may be kept under 2 to 4 atm pressure and $H_2$ may be added. Alternatively, biomass may be degraded, anaerobically to produce methane and $CO_2$ or other products (e.g. ethanol), or aerobically (e.g. beer). The pressure may be decreased to increase digestion rate. The removed gases may be transferred to a reducing reactor and pressurized to facilitate the reaction. Yet another alternative is to use a batch culture wherein the degrading step precedes the reducing step in the same reactor, and the conditions are optimized for both steps, for example by controlling pressures and supplementing or removing gases or other products.

Thus, the present invention comprises a process to rapidly grow microorganisms, optionally under aerobic conditions, using unwanted biomass substrates. $CO_2$ and optionally $H_2$ released from the process as well as additional gas (e.g. CO, $CO_2$, $H_2$) are added and pressurized to make it thermodynamically feasible to convert CO, or $CO_2$ and $H_2$ to desired organic products such as alcohols or acids. With these conditions that make it thermodynamically feasible to make a high concentration of the desired products, and with microorganisms that can tolerate high concentrations of the products, and can use grow on unwanted biomass substrates, and with the ability to convert CO or CO2 and H2 to desired products, the desired products are produced. A consortium of microorganisms can be used including members of the genera: *Citrobacter, Klebsiella, Escherichia, Enterococcus*, among others.

Thermodynamics

The inventor discovered that microbial fermentation is controlled, to a large extent, by the second law of thermodynamics. This principle enables the present invention. The second law of thermodynamics states that a reaction cannot proceed spontaneously unless the change in Gibbs free energy ($\Delta G$) is negative. An organism can only obtain energy by carrying out a reaction if the $\Delta G$ is negative, and therefore since one can calculate $\Delta G$ from concentrations and pressures in the fermentation, one can calculate the conditions necessary for an organism to survive or grow from a desired conversion by calculating the $\Delta G$ for that conversion under different conditions.

For conversion of any reactant (or substrate) to any product or products, the change in Gibbs free energy ($\Delta G$) must be less than 0 for all linked reactions. When organisms need to take a step in a reaction in which the $\Delta G$ is positive, that step must be coupled with another reaction that is more negative than the positive reaction is positive, so that the sum of both reactions is negative. For example, the $\Delta G$ for many steps in metabolic pathways is positive without considering linked reactions, but another chemical reaction such as ATP hydrolysis to ADP is linked to the steps with positive ΔG so the overall step is negative. However, in order to continue carrying out the reaction, the organism must use energy obtained somewhere else to regenerate ATP. Therefore, catabolic pathways used to generate energy for the organism must have net negative ΔG, and preferably be negative enough to enable the organism to capture energy (e.g. generate ATP). The inventor discovered that conditions of the fermentation could be manipulated to make it thermodynamically feasible to degrade organic products to gases, and conversely different conditions enable making desired products from gases. In one set of conditions, organisms that can degrade the products grow, and in another set of conditions, organisms that synthesize the products grow.

In the context of the entire microbial metabolism, an organism can obtain energy from a process only if the overall ΔG for the process is negative. Thus, calculating ΔG for a desired chemical pathway in gas fermentations enabled the inventor to define conditions wherein a microorganism could obtain energy to survive by carrying out desired reactions. For example, it is necessary to provide certain partial pressures of gases to the fermentation to make it feasible to produce desired concentrations of organic products; higher gas pressures enable higher product concentrations from gases.

For example, most heterotrophic organisms can obtain energy by degrading glucose because glucose is a high-energy compound. Aerobic organisms can generate up to 38 ATP from ADP by completely oxidizing a glucose molecule to $CO_2$ and $H_2O$. Anaerobic organisms can generate less ATP because they cannot use $O_2$ to completely oxidize the glucose, but instead partially degrade it to an alcohol or acid or other organic product. In either case, the ΔG for glucose degradation is highly negative. In an aerobic environment, the ΔG for degradation of the organic products to $CO_2$ and $H_2O$ is also highly negative so aerobic organisms can degrade the anaerobic fermentation products. For that matter, fuels that are produced as anaerobic products (e.g. alcohols) can also be burned in vehicles because much energy remains by oxidizing the fuels with air even after they have reached nearly the lowest energy state under anaerobic conditions. However, synthesis of organic products from $CO_2$ and $H_2$ or other low-energy products requires input of energy in aerobic conditions. An organism might be able to use ATP to support a desired chemical reaction, but if the organism uses ATP, it will not obtain energy from the reaction or grow from the reaction. Some organisms can grow from the energy they obtain by converting CO, or $CO_2$ and $H_2$ to organic products. These organisms can only grow when the pressure of the gases is high relative to the concentration of organic product. Thus, one aspect of the present invention is providing conditions to the fermentation to make it possible for organisms that produce desired organic products to grow from the energy they obtain by converting the gases, such as CO, or $CO_2$ and $H_2$, to desired organic products. This means providing high pressures of gaseous reactants and optimal ratios of gases. Exactly how high the pressures need to be depends on numerous factors: e.g. product concentration or desired concentration, temperature, pH, and concentration of other substrates and co-products, as well as which reactants are to be converted to which products.

Conveniently, it is not difficult to calculate exactly what the conditions are to make it thermodynamically feasible to produce a certain product. The tools needed are taught in high-school chemistry and algebra. First, the desired conversion must be expressed as a balanced chemical equation. For example: $2CO_2 + 4H_2 \leftrightarrow CH_3COO^- + +2H_2O$.

The ΔG can then be determined for the reaction using algebra in two steps. First, determine the ΔG° for the reaction under standard conditions. This can be done by subtracting the Gibbs energy in the products from that in the reactants. And then finding the ΔG for the actual conditions by solving the equation $\Delta G = \Delta G° + \text{Ln}\{[\text{products}]/[\text{reactants}]\}$, where [products] and [reactants] are the activities of the reactants and products (at dilute concentrations roughly equal to the concentrations). This can be done for any set of reactants and products and in fact was done for several fermentation products under many sets of conditions by the inventor (U.S. Pat. No. 8,178,329 issued May 15, 2012, and U.S. patent application Ser. No. 13/381,127 filed Dec. 28, 2011) which are incorporated in their entirety by reference). Thus, calculating the conditions that make it thermodynamically feasible for a reaction is an objective process and does not require any experimentation. Describing a process in terms of setting up a set of conditions to make it thermodynamically feasible is similar to providing a recipe that calls for certain oven temperature, and baking for a specified time perhaps as a function of the size of a roast. Although calculations may be necessary or a table referred to, no experimentation is required if the parameters are available. When the inventor teaches that the conditions of the fermentation for conversion of a set of reactants to a set of products make it thermodynamically feasible to produce the product from the reactants, he teaches the use of a specific set of calculations to determine necessary conditions for the fermentation. However, many different combinations of conditions can be used, and therefore it is not feasible to simply provide temperatures and pressures that correspond to all potential desired products and all possible substrates. Generally, one wishes the reaction to be a bit beyond thermodynamically feasible with ΔG more negative to provide greater energy for the organism to grow or maintain itself, but clearly the organism will not be able to grow if the reaction it carries out to sustain itself is not thermodynamically feasible.

In the present specification, the inventor teaches that specified microorganisms can be used to produce organic products from CO, or $CO_2$ and $H_2$ when it is thermodynamically feasible to produce the products. In addition, the inventor teaches that growing organisms that degrade certain organic substances to $CO_2$ and $H_2$ requires a different set of conditions wherein it is thermodynamically feasible to degrade the organic substances to $CO_2$ and $H_2$.

In the context of this disclosure, thermodynamically feasible reactions are defined to mean the ΔG is less than 0 for the over all reaction, without any additional energy source generated or used. The degree that the ΔG is less than 0 indicates how much energy can be captured by the microorganisms. If a reaction occurs with positive ΔG, it indicates how much energy must be used from other sources to allow the reaction. However, where it is said that conditions are used to make it thermodynamically feasible to carry out a pathway (e.g. produce a certain product from a certain set of substrates), it is assumed that conditions are calculated to make it thermodynamically feasible, or ΔG less than 0, for the overall reaction pathway without considering ATP or other potentially linked reactions unless otherwise stated. This can be seen from context as the ΔG calculations are performed to determine conditions where the reactions can occur in a way to release energy for microbial maintenance or growth.

Process to Calculate Free Energy and Equilibrium Concentrations

A mathematical model defined in a spreadsheet is used to determine the change in free energy for different reactions that may occur in fermentation. The model may be modified by adding or subtracting reactions as warranted by different types of fermentation. In addition, the free energy change for reactions can be determined for different conditions (e.g. temperature, pressure, pH, concentrations of metabolites, pressures of gases). In addition, the equilibrium concentrations or equilibrium ratios of metabolites can also be determined. The description that follows provides the information necessary to create the model, or a similar model for different metabolites that can be included.

The balanced reactions giving rise to each potential product from the biomass source are first determined. For example, acids, alcohols and alkanes like methane can be derived ultimately from $CO_2$ and $H_2$. The stoichiometry is determined by balancing each reaction so that equal numbers of carbon, hydrogen, oxygen and so forth are on each side of the equation.

For example,

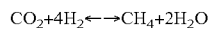
$$CO_2 + 4H_2 \leftrightarrow CH_4 + 2H_2O$$

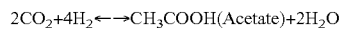
$$2CO_2 + 4H_2 \leftrightarrow CH_3COOH(\text{Acetate}) + 2H_2O$$

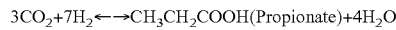
$$3CO_2 + 7H_2 \leftrightarrow CH_3CH_2COOH(\text{Propionate}) + 4H_2O$$

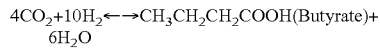
$$4CO_2 + 10H_2 \leftrightarrow CH_3CH_2CH_2COOH(\text{Butyrate}) + 6H_2O$$

$$2CO_2 + 6H_2 \leftrightarrow CH_3CH_2OH(\text{Ethanol}) + 3H_2O$$

$$3CO_2 + 9H_2 \leftrightarrow CH_3CH_2CH_2OH(\text{1-propanol}) + 5H_2O$$

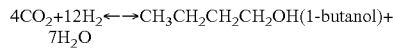
$$4CO_2 + 12H_2 \leftrightarrow CH_3CH_2CH_2CH_2OH(\text{1-butanol}) + 7H_2O$$

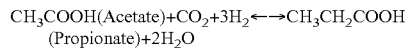
$$CH_3COOH(\text{Acetate}) + CO_2 + 3H_2 \leftrightarrow CH_3CH_2COOH(\text{Propionate}) + 2H_2O$$

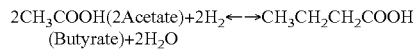
$$2CH_3COOH(\text{2Acetate}) + 2H_2 \leftrightarrow CH_3CH_2CH_2COOH(\text{Butyrate}) + 2H_2O$$

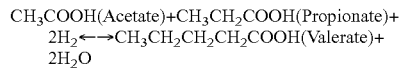
$$CH_3COOH(\text{Acetate}) + CH_3CH_2COOH(\text{Propionate}) + 2H_2 \leftrightarrow CH_3CH_2CH_2CH_2COOH(\text{Valerate}) + 2H_2O$$

Thus, the balanced equations can be determined even without knowledge of the exact pathway. The respective pathways are determined for any and every reaction thought to occur in the fermentation system of interest. Which reactions occur can be assumed based on what products accumulate or are otherwise found in the fermentation.

The $\Delta G$ for any pathway depends on which products and reactants are produced, and therefore different conditions are needed to make each reaction thermodynamically feasible. The change in Free Energy under standard conditions ($\Delta G^\circ$) is determined in the established way of calculating the Free Energy of Formation from the basic elements for each reactant and product and subtracting the Free Energy of Formation of the products from the Free Energy of Formation of the reactants (Chang, R. 1981. Physical Chemistry with Applications to Biological Systems: Second Edition, MacMillan Publishing Co., Inc., New York, which is incorporated herein by reference). For the current patent application, the free energy of formation values not found in the book authored by Chang were obtained from the literature (Guthrie, J. Peter; 1992. A group equivalents scheme for free energies of formation of organic compounds in aqueous solution. Canadian J. Chemistry 70:1042-1054 which is incorporated herein by reference). Some relevant values from the literature are provided again in Table 1. Similar information can be obtained from these references and others if desired to add other metabolites to the model.

The values in Table 1 are the key thermodynamic data under standard conditions for these reactants and products as well as some other important potential fermentation intermediates. These values represent the free energy of formation ($\Delta G^\circ_f$) and enthalpy of formation ($\Delta H^\circ_f$) of the metabolites from the elements (e.g. $H_2$, $O_2$, graphite). Free energy) ($\Delta G^\circ$ and enthalpy)($\Delta H^\circ$ under standard conditions and concentrations can be determined from these tabular values for each reaction of interest (Chang, 1981 as cited). Standard conditions are 1 M concentration of each soluble reactant and product, $1.01325 \times 10^5$ Pa (1 atm) of all gases, and 298.15 K.

$$\Delta G^\circ = \Delta G^\circ_f \text{ of products} - \Delta G^\circ_f \text{ of reactants, and}$$

$$\Delta H^\circ = \Delta H^\circ_f \text{ of products} - \Delta H^\circ_f \text{ of reactants}$$

Adjustment to each $\Delta G^\circ$ for temperature can be made using a transformation of the van't Hoff equation and enthalpy where $T_1$ and $T_2$ are the initial and final temperatures respectively, and $\Delta G^\circ$, and $\Delta G^\circ$, are the respective standard free energy values:

$$\Delta G^\circ_{T2} = T_2/T_1[\Delta G^\circ_{T1} - \Delta H^\circ(T_2 - T_1)/T_2]$$

So, for example the $\Delta G$ at 39° C. or 312 K was determined for many of the reactions of interest from the tabular data reported at 298.15 K because the fermentations were conducted at 312 K.

Once the $\Delta G^\circ$ is determined, it can be used to calculate the actual $\Delta G$ for a specific set of conditions using the equation:

$$\Delta G = \Delta G^\circ + RT \ln \{[\text{products}]/[\text{reactants}]\}$$

where the [products] and [reactants] is concentration of all products or reactants in the fermentation, T is temperature in degrees Kelvin. For the current studies temperature was usually set to 312 K. R is the gas constant=0.00831 kJ/K. Given the value of $\Delta G$, the free energy available for a reaction can be shown. If the $\Delta G$ is negative, there would be energy for organisms to produce ATP and grow while carrying out the process. If the $\Delta G$ is positive, the opposite reaction might enable organisms to obtain energy. Generally, about 44 kJ/mol is required for fermentation organisms to produce a mole of ATP, but many organisms and reactions can produce a fraction of an ATP and the exact requirement for free energy depends on energy status of the organisms and other factors.

TABLE 1

Thermodynamic data of selected compounds.

| Substance | $\Delta H_f^\circ$ | $\Delta G_f^\circ$ |
|---|---|---|
| Methane (g) | −74 | −50 |
| Ethane (g) | −84 | −32 |
| Methanol (aq) | −201 | −176 |
| Ethanol (aq) | −235 | −182 |
| 1-Propanol (aq) | −255 | −173 |
| 2-Propanol (aq) | −273 | −186 |
| 1-Butanol (aq) | −275 | −163 |
| 2-Methyl-1-propanol (aq) | −284 | −167 |
| 2-Butanol (aq) | −293 | −179 |

TABLE 1-continued

Thermodynamic data of selected compounds.

| Substance | $\Delta H_f°$ | $\Delta G_f°$ |
|---|---|---|
| 1-Pentanol (aq) | −294 | −153 |
| Acetoaldehyde (aq) | −166 | −140 |
| Acetic acid (aq) | −432 | −394 |
| Propionic acid (aq) | −453 | −385 |
| Butyric acid (aq) | −475 | −378 |
| Valeric acid (aq) | −491 | −365 |
| Caproic acid (aq) | −511 | −386 |
| Glucose (aq) | −1264 | −917 |
| $CO_2$ (g) | −413 | −386 |
| $H_2$ (g) | 0 | 0 |
| Water (l) | −286 | −237 |

Free energy in kJ per mole under standard conditions of several potential fermentation metabolites at 298.15 K and $1.01325 \times 10^5$ Pa (1 atmosphere). Standard conditions are 1 M concentration of each soluble reactant and product, $1.01325 \times 10^5$ Pa (1 atm) of all gases, and 298.15 K.

It is possible to calculate the $\Delta G$ for any reaction for conversion of $H_2$ and $CO_2$ to any organic compound using the procedure just described. Therefore, different sets of conditions can be established for degrading any organic compound to $H_2$ and $CO_2$, or for synthesizing the organic compound from $H_2$ and $CO_2$. Using these conditions makes it possible to use the invention as described to isolate and use microorganisms and process conditions to produce organic products. Nearly every organic compound is degraded by microorganisms in the environment, and under conditions that make it thermodynamically favorable, nearly every organic compound is synthesized by microbes. Therefore, the present invention enables isolation and use of microorganisms for production of many different products.

Example $\Delta G$ Calculations

The calculated $\Delta G$ values for three reactions important to fermentation and synthesis from gases are shown in FIG. 1. In this example, a constant total pressure of 1 atm was maintained, but the ratio of $H_2$ to $CO_2$ increased. At the left end of the graph, typical conditions in an anaerobic fermenter or the rumen of the cow are shown. Note that the $\Delta G$ for methane synthesis from $4H_2$ and 1 $CO_2$ is about −50 kJ/mol of methane produced. Therefore, it would be possible to produce about 1 ATP per methane. The corresponding $\Delta G$ for acetate or ethanol synthesis from $H_2$ and $CO_2$ are positive. While the $\Delta G$ for acetate synthesis is near 0, that for ethanol synthesis is strongly positive (+75 kJ/mol). Under these conditions, ethanol can be converted to acetate or might be degraded to $CO_2$ and $H_2$. As the $H_2$ to $CO_2$ ratio increases, the $\Delta G$ for methane continues to decrease and then begins to slowly increase. The minimum value occurs at a ratio of 4:1 $H_2$ to $CO_2$ on a molar basis or volume basis. At the minimum, nearly 3 ATP could be generated per mol of methane rather than one. This explains why methanogens grow faster under these conditions. In addition, as the ratio of $H_2$ to $CO_2$ increases, it also becomes thermodynamically feasible to produce acetate from $CO_2$ and $H_2$. The minimum value occurs at a ratio of 2:1 $H_2$ to $CO_2$, and it is possible to produce more than one mole ATP per mole at this ratio. The $\Delta G$ for ethanol synthesis decreases as well until it reaches a minimum at a ratio of 3:1 $H_2$ to $CO_2$. Wherein the $\Delta G$ for ethanol synthesis initially decreases faster than for acetate synthesis, and the $\Delta G$ for both acetate and ethanol decline faster than for methane, the curves converge as the ratio increases toward the minimum. Thus, near the minimum, it becomes possible to make all of the products. After reaching the minimum $\Delta G$, the curves for acetate and ethanol increase faster than for methane, making it more favorable to produce methane than the other two as the $H_2$ to $CO_2$ ratio increases further.

It is clear from this graph why methane is the favored product under typical fermentation conditions and why methane is especially favored at low or high ratio of $H_2$ to $CO_2$. If the fermentation is designed to degrade acetate to methane and $CO_2$, either a low or a high ratio of $H_2$ to $CO_2$ is required. Furthermore, acetate and ethanol are only produced when there is both $H_2$ and $CO_2$ present.

Figure 2:
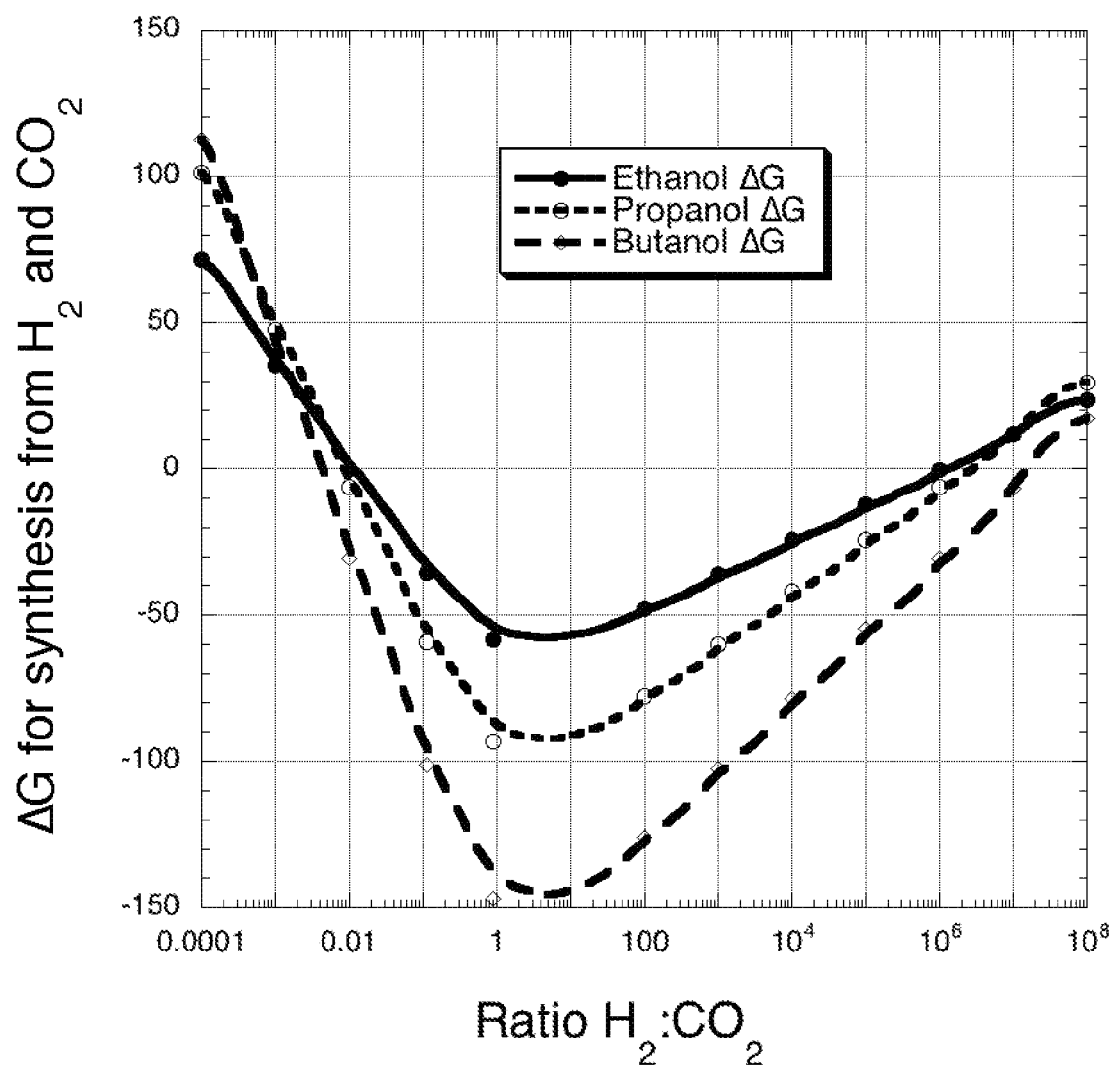
FIG. 2. The change in free energy ($\Delta G$; kJ/mol) for synthesis of alkyl alcohols from $H_2$ and $CO_2$ as the molar ratio of $H_2$ to $CO_2$ increases. This figure shows that energy for forming alcohols is greatest for longer alcohols at the ratio for maximal synthesis (3:1 for $H_2$ to $CO_2$), but otherwise shorter alcohols are favored over longer alcohols.
Figure 3:
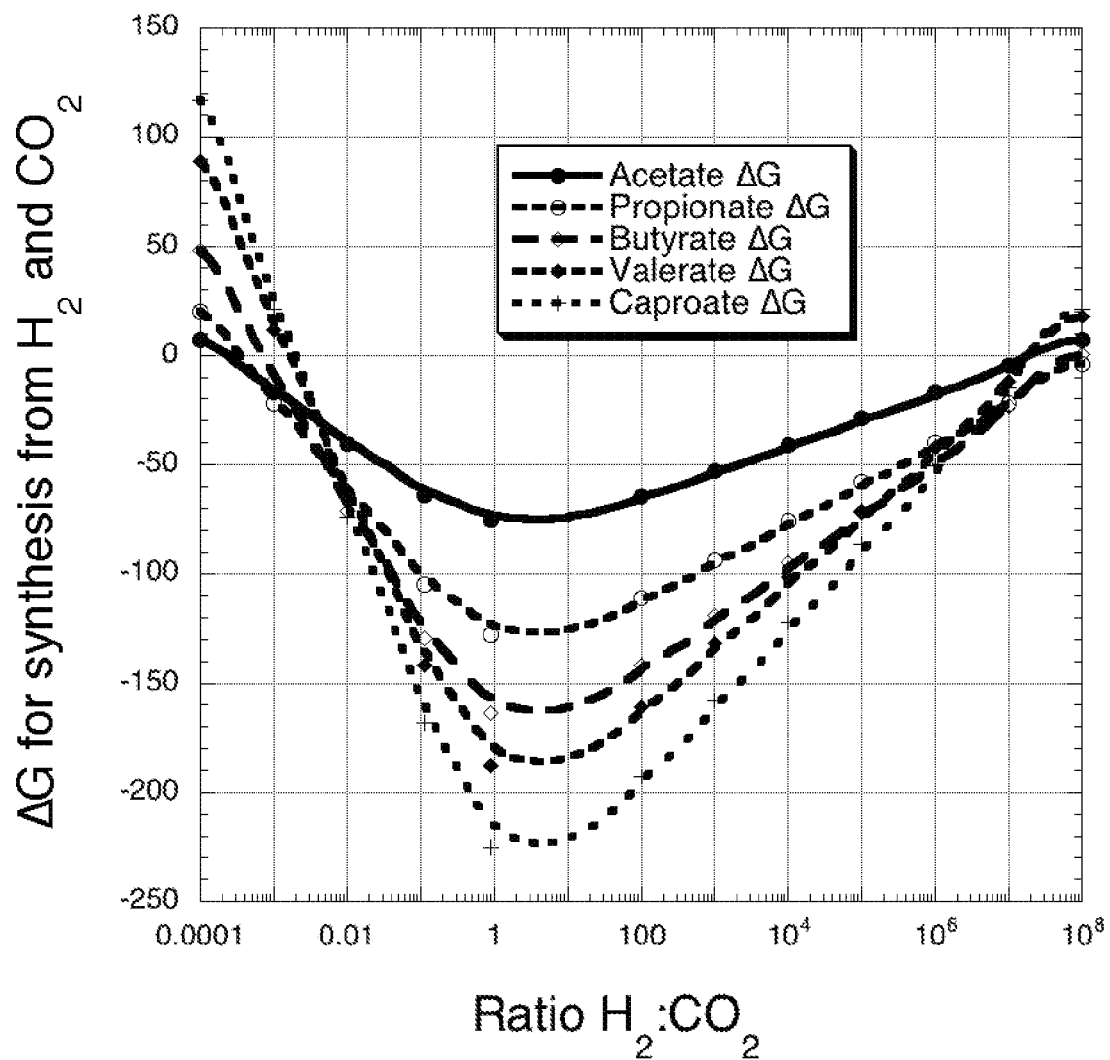
FIG. 3. The change in free energy ($\Delta G$; kJ/mol) for synthesis of carboxylic acids ($C_2$ to $C_6$) from $H_2$ and $CO_2$ as the molar ratio of $H_2$ to $CO_2$ increases. This figure shows the increase in energy available to make longer carboxylic acids at the ratio for maximal synthesis (between 2:1 to 3:1 for $H_2$ to $CO_2$), but that shorter carboxylic acids are favored at both lower and higher ratios of $H_2$ to $CO_2$.

The $\Delta G$ for production of ethanol, propanol, and butanol are shown in FIG. 2. Initially, production of alcohol is not feasible under the conditions shown on the far left side of the graph. As the $H_2$ to $CO_2$ ratio increases, first butanol, then propanol, and finally ethanol cross the line Y=0 representing thermodynamic feasibility. At $H_2$ to $CO_2$ ratio of 3:1, each $\Delta G$ is minimized with the longer alcohols more favored than the shorter ones. Thus, conditions of a ratio of 3:1 favor any alcohol production with enough energy left over for ATP production. The same conditions for carboxylic acid production are shown in FIG. 3. In this case, acetate is the first to become thermodynamically feasible, but as the $H_2$ to $CO_2$ ratio increases longer-chain carboxylic acids also become feasible, with the longer acids more favored than the shorter ones.

These data show how to establish conditions for synthesis of alcohols (including longer-chain alcohols) or carboxylic acids from $H_2$ and $CO_2$. Where one wants to degrade the organic compounds to $CO_2$ and $H_2$, highly positive $\Delta G$ would be used.

There are several ways in which the thermodynamic analysis shows it is possible to shift metabolism toward synthesis of a desired alcohol or acid. The first way is to change the pressure of all gases, for example to increase total gas pressures, so that the partial pressure of $CO_2$ and $H_2$ are affected. Increasing the partial pressure of all gases this way increases the concentration to which alcohols or acids can be synthesized from gases. Decreasing the partial pressure of all product gases increases the degradation of acetic acid or ethanol. The second way to increase synthesis of alcohols or acids is to adjust the ratio of synthesis gases to a ratio that favors a certain product, the higher ratio favoring alcohols over acids and longer-chain length acids or alcohols over the shorter.

Calculations of $\Delta G$ or equilibrium calculations can be used to quantify the effect of the ratio of $H_2$ to $CO_2$, the total pressure, and pH. The second law of thermodynamics enables calculation of which direction a pathway flows and whether energy is required or can be captured by carrying out the reaction. The relationship is determined by the sign and magnitude of the change in free energy ($\Delta G$) from the equation: $\Delta G = \Delta G° + RT \ln \{[Products]/[Reactants]\}$ where [Products] or [Reactants] represents the multiplicative product of the concentrations or partial pressures of solutes or gases and $\Delta G°$ is constant for each reaction based on the products and reactants. When the $\Delta G$ is negative, the reaction can proceed and if it is negative enough, ATP can be generated.

The same principles can be applied to mixtures of $H_2$ and carbon monoxide (CO). Similar calculations based on stoichiometry can be used to quantify that the ratio of $H_2$ to CO for maximal synthesis is 2:1 for ethanol or 1:1 for acetic acid. The effect of increasing pressure is the same as for synthesis of ethanol or acetic acid from $H_2$ and $CO_2$. Thus, adjusting gas formulations and increasing pressures would also shift metabolism toward greater ethanol synthesis or acetic acid synthesis when using CO and $H_2$ as well, or when selecting for microorganisms that can use these gases. The inventors discovered that organisms selected to produce products from $CO_2$ and $H_2$ produced a similar profile of products from CO and $H_2$.

Just as the conditions to favor synthesis of alcohols of different length were established through the previous analysis, the approach can also be applied to produce volatile fatty acids (e.g. $C_2$ to $C_5$), or even longer-chain carboxylic acids. The ΔG values shown in FIG. 3 demonstrate the potential for producing carboxylic acids of increasing length by using a ratio of $H_2$ to $CO_2$ to make production of desired carboxylic acids feasible or more favorable than competing products. The minimal ΔG for acetate production from $H_2$ and $CO_2$ occurs at 2:1 $H_2$ to $CO_2$ ratio, but the minimal ΔG for longer carboxylic acids occurs at a slightly higher ratio (up to 3:1). The thermodynamics of longer carboxylic acids is also favored by increasing total pressure and lower pH favors longer chain acids over the shorter ones. These are precisely the conditions in which organisms that mainly produce longer chain acids like butyrate and iso-valerate were isolated.

SPECIFIC EXAMPLES

In the specific examples below, media were prepared as indicated previously and all incubations were at 39° C. unless otherwise stated. Production of acids, alcohols, and gases were measured using gas chromatography as described previously.

Example Isolates

Many genera of gram-positive (e.g. *Clostridium, Enterococcus*) and gram-negative (*Citrobacter, Klebsiella, Escherichia, Salmonella*) bacteria are known to be tolerant to high concentrations of alcohols (e.g. >6%) or acids (>2%), and are known to make alcohols or acids. The present inventor discovered that these acid-tolerant and alcohol-tolerant microorganisms can use the gases $CO_2$, CO and $H_2$ or other intermediates that can be converted to these products (e.g. $HCO_3^-$, $H_2S$, $Fe^{++}$) to produce high concentrations of alcohols or acids. For example, several bacteria were isolated and grown in broth with greater than 6% ethanol and greater than 2% mixed VFA under more than 1:1 ratio of $H_2:CO_2$ or $H_2$: CO. Even more preferably the ratio of $H_2:CO_2$ or $H_2$: CO was greater than 3 or 2 respectively, and the gas pressures were greater than 4 or 8 atmospheres. Especially when the gas pressures exceed an atmosphere, it becomes thermodynamically favorable to convert the gases to higher concentrations of alcohols or acids so greater concentrations of alcohols or acids are produced. As the ΔG for the reactions becomes more negative with greater pressures of the $CO_2$, CO and $H_2$, the microbes can capture more Gibbs energy and grow faster and produce the products faster as well. Microbes that use other sources of biomass (e.g. glucose, cellobiose, cellulose, plant fiber) to produce alcohols or acids, shift fermentation to produce greater concentrations of the alcohols or acids from the biomass at greater rates when the partial pressures of the gases increase. This increase in pressure, increases the energy the microbes can capture by producing the alcohols or acids, and decreases the energy they capture by producing gases, thus shifting the fermentation from producing gases to producing VFA and alcohols from gases.

One example isolated microorganism used gases, grew (increased optical density), and produced ethanol even when concentration of ethanol was greater than 6% by volume when either CO or $CO_2$ was the sole carbon source, as long as the environment was highly reduced by providing CO pressure or added $H_2$ under pressure starting at 2 or 3 atm. The strain also used gases and grew in broth with both 6% ethanol and 20 g/L of a mixture of volatile fatty acids (equimolar acetate, propionate, and butyrate) under similar conditions of headspace pressure and gas composition. This strain was comprised of gram-negative rods that grew aerobically or under $N_2$ (without added $H_2$) on glucose or citrate as the only carbon source, again producing ethanol and VFA. The strain could also grow aerobically when ethanol was the only carbon source. A segment of rRNA was amplified with PCR and sequenced. Its 16S rRNA was 99% identical to a previously sequenced strains of *Citrobacter koseri*. It was also greater than 97% homologous to previously sequenced strains of *Klebsiella, Escherichia*, or *Salmonella*, among others; however it was biochemically different from *Salmonella* and *Escherichia* (i.e. it grew on citrate-only medium). A segment of 16S rRNA sequence is as follows:

```
                                               Seq. 1.
gctgcttcgc tgacgagtgg cggacgggtg agtaatgtct gggaaactgc ctgatggagg gggataacta ctggaaacgg tagctaatac cgcataacgt cgcaagacca aagaggggga gcttcgggcc tcttgccatc agatgtgccc agatgggatt agcttgttgg tggggtaacg gctcaccaag gcgacgatcc ctagctggtc tgagaggatg accagccaca ctggaactga gacacggtcc agactcctac gggaggcagc agtggggaat attgcacaat gggcgcaagc ctgatgcagc catgccgcgt gtatgaagaa ggccttcggg ttgtaaagta ctttcagcgg ggaggaaggt gttgtggtta ataaccgcag caattgacgt tacccgcaga agaagcaccg gctaactccg tgccagcagc cgcggtaata cggagggtgc aagcgttaat cggaattact gggcgtaaag cgcacgcagg cggtctgtta agtcagatgt gaaatccccg ggctcaacct gggaactgca tctgatactg gcaggcttga gtctcgtaga g
```

A strain grew on $CO_2$ (and $HCO_3^-$) or CO as the only carbon source by using the gases, and it produced ethanol to greater than 6% concentration when grown under 2 to 4 atmospheres $CO_2$ and $H_2$ pressure. It also grew aerobically on glucose but not on citrate as a sole carbon source. Its 16s rRNA (Seq. 2) was 98% identical to a previously isolated organism identified as *Escherichia coli* or *E. Furgusonii*, and was greater than 97% identical to *Klebsiella* or *Citrobacter*, but this strain did not grow on citrate medium thus ruling out *Klebsiella* and *Citrobacter*. A segment of 16S rRNA sequence is as follows:

```
                                               Seq. 2
tgagtaatgt ctgggaaact gcctgatgga gggggataac tactggaaac ggtagctaat accgcataac gtcgcaagac caaagagggg gaccttcggg cctcttgcca tcggatgtgc ccagatggga ttagcttgtt ggtggggtaa cggctcacca aggcgacgat ccctagctgg tctgagagga tgaccagcca
```

-continued

```
cactggaact gagacacggt ccagactcct acgggaggca gcagtgggga atattgcaca atgggcgcaa gcctgatgca gccatgccgc gtgtatgaag aaggccttcg ggttgtaaag tactttcagc ggggaggaag gtgttgaggt taataacttt gccaattgac gttacccgca gaagaagcac cggctaactc cgtgccagca gccgcggtaa tacgagggt gcaagcgtta atcggaatta ctgggcgtaa agcgcacgca ggcggtttgt taagtcagat gtgaaatccc cgggctcaac ctgggaactg catctgatac tggcangctt gagtctcgta ga
```

A strain grew very rapidly on $CO_2$ and $H_2$ as the only carbon substrate, and decreased gas pressure, and produced ethanol when in broth medium with 6% ethanol but did not produce significant acid. This strain did not take up carbon monoxide or grow well on carbon monoxide. It also grew aerobically on citrate or glucose as the only carbon source. The 16S rRNA was 99% homologous with a sequenced strain of *Klebsiella oxytoca*, and approximately 99% homology with Enterobacteriaceae family, *Enterobacter aerogenes, Pectobacterium, Citrobacter*, and *Serratia* among others.

Seq 3.
```
gggcggtgtg tacaaggccc gggaacgtat tcaccgtggc attctgatcc acgattacta gcgattccga cttcatggag tcgagttgca gactccaatc cggactacga catactttat gaggtccgct tgctctcgcg aggtcgcttc tctttgtata tgccattgta gcacgtgtgt agccctactc gtaagggcca tgatgacttg acgtcatccc caccttcctc cagtttatca ctggcagtct cctttgagtt cccgaccgaa ccgctggcaa caaaggataa gggttgcgct cgttgcggga cttaacccaa catttcacaa cacgagctga cgacagccat gcagcacctg tctcagagtt cccgaaggca ccaaagcatc tctgctaagt tctctggatg tcaagagtag gtaaggttct tcgcgttgca tcgaattaaa ccacatgctc caccgcttgt gcgggccccc gtcaattcat ttgagtttta accttgcggc cgtactcatg tctgggaaac tgcccgatgg aggggataa ctactggaaa cggtagctaa taccgcataa cgtcgcaaga ccaaagaggg ggaccttcgg gcctcttgcc atcggatgtg cccagatggg attagctagt aggtgggta acggctcacc taggcgacga tccctagctg gtctgagagg atgaccagcc acactggaac tgagacacgg tccagactcc tacgggaggc agcagtgggg aatattgcac aatgggcgca agcctgatgc agccatgccg cgtgtatgaa gaaggccttc gggttgtaaa gtactttcag cgaggaggaa ggtgttgtgg ttaataaccg cagcgattga cgttactc
```

Example Gram Positive Bacteria

Several bacterial species were isolated using media with 1-2% tryptic digest of casein and/or 1-2% yeast extract, but otherwise as described above. In this case, several Gram-positive bacteria were isolated that could convert $CO_2$, CO and $H_2$ to at least 6% ethanol, and also to iso-butanol or n-butanol. Isolated bacteria were identified based on 16S rRNA and found not to be dissimilar from various strains of *Clostridium* or *Enterococcus*. For example, 16S rRNA was >97% homologous with *Clostridium* spp. and other strains were more than 97% homologous with *Enterococcus gallus, E. casselflavous, E. faecium*, or *E. faecalis*. A mixed culture of *Clostridium* and *Enterococcus faecium* produced greater than 5% ethanol from $CO_2$ and $H_2$ over 10 to 14 days starting from medium without ethanol.

Example Citrate- and Glucose-Using Bacteria that Use CO and $H_2$.

Several strains of bacteria were isolated on agar plates placed in pressure cookers with no carbon sources other than BACTOAGAR® (which was not used by the bacteria) and CO in the pressure cooker headspace. Initial pressure was 2 atm with only CO, or other treatments included up to 10 atm CO in steel chambers. Other treatments used H2 and CO in the headspace.

The isolates were grown in broth medium with 6% ethanol and no other carbon sources except when CO gas was included at 4 atm pressure in the tube, and at times these pressurized tubes were in turn incubated inside pressure cookers at 2 atmospheres pressure of the same gas composition. Strains decreased gas in the headspace of the tubes to less than the pressure in the pressure cooker headspace, thus verifying that gas was used internally and did not simply leak out of the tubes. Optical density increased to indicate growth for 1-2 days, and then stabilized. Ethanol concentration increased about 0.5% above original within 10 to 14 days. Higher concentrations could be obtained by adding additional gas once the headspace gas was depleted. Agar plates containing citrate or glucose as the only carbon source (when agar was not degraded) were inoculated with broth from each tube, and incubated at 38° C. in open air. Colonies formed within 10 hours for some strains on citrate or glucose under aerobic conditions. These colonies were used to re-inculate broth medium and the colonies continued producing ethanol from syngas when transferred. Thus, the inventors demonstrated that aerobic microorganisms could grow and produce ethanol under anaerobic conditions from CO or $CO_2$ as the only source of carbon, and from $H_2$.

Fiber Digestion by Bacteria that Use Gases

An isolated strain of bacterium that had 16S rRNA similar to *Citrobacter koseri* (similar to Seq. 1), which grew aerobically on citrate medium, was incubated to medium as described with 1% dry matter weight timothy hay. Gas headspace was 1 atmosphere $CO_2$ and 1 atmosphere $H_2$. Volatile fatty acids and alcohols were measured after 48 h. After incubation, acids and VFA were measured by gas chromatography, and were acetate (1.2 g/L), propionate (0.20 g/L), butyrate (0.13 g/L), and isovalerate (0.03 g/L). In addition, greater than 0.04% ethanol and smaller quantities of 1-propanol were measured by gas chromatography. The residue was analyzed for neutral detergent fiber by boiling in pH 7 detergent for 1 hour and filtering. The remaining dry fiber residue was less than 80% as much as for samples that had not been inoculated. Thus, the strain was able to digest plant fiber and produce alcohols or long-chain volatile fatty acids from ligno-cellulose or plant fiber. This strain also produced similar products from gases alone when incubated with $H_2$ and $CO_2$ in medium without biomass. The rRNA sequence for the strain is provided below. It was 100% homologus with a previously identified strain of *Citrobacter koseri*, and had greater than 97% homology with *Escherichia fergusonii*, *E. coli*, *Shigella boydii*, *S. sonnei*, *S. boydii*, among others. However, it was only aligned with Seq. 1 over about 23% of the length.

```
                                                     Seq. 4
    tccgtggatg tcaagaccag gtaaggttct tcgcgttgca tcgaattaaa ccacatgctc caccgcttgt gcgggccccc gtcaattcat ttgagtttta accttgcggc cgtactcccc aggcggtcga cttaacgcgt tagctccgga agccacgcct caagggcaca acctccaagt cgacatcgtt tacggcgtgg actaccaggg tatctaatcc tgtttgctcc ccacgctttc gcacctgagc gtcagtcttc gtccagggg ccgccttcgc caccggtatt cctccagatc tctacgcatt tcaccgctac acctggaatt ctaccccct ctacgagact caagcctgcc agtatcagat gcagttccca ggttgagccc gggatttca catctgactt aacagaccgc ctgcgtgcgc tttacgccca gtaattccga ttaacgct
```

A different strain that was identified as having 16S rRNA homology (>98%) with *Enterococcus faecalis*, which was incubated for 48 h under similar conditions to the previous example and produced acetate (0.7 g/L), propionate (0.25 g/L), isobutyrate (0.23), butyrate (0.17 g/L), isovalerate (0.36 g/L), and valerate (0.25 g/L). It also produced 2 g/L ethanol, and lesser amounts of 1-butanol and iso-butanol. This bacterium also used $H_2$ and $CO_2$ from headspace gases and grew and produced acids and alcohols under reducing conditions ($H_2$ pressure greater than 1 atm) with minimal source of organic carbon (e.g 0.1% tryptic digest of casein). The 16S-rRNA sequence for the *Enterococcus* is shown below. It was 100% homologous with a sequence from *Enterococcus faecalis*, *E. caninintestini*, and *E. dispar*, and more than 97% aligned with several *Enterococcus* species or other gram-positive species.

```
                                                     Seq. 5.
    cggctaacta cgtgccagca gccgcggtaa tacgtaggtg gcaagcgttg tccggattta ttgggcgtaa agcgagcgca ggcggtttct taaqtctgat gtgaaagccc ccggctcaac cggggagggt cattggaaac tgggagactt gagtgcagaa gaggagagtg gaattccatg tgtagcggtg aaatgcgtag atatatggag gaacaccagt ggcgaaggcg gctctctggt ctgtaactga cgctgaggct cgaaagcgtg gggagcaaac aggattagat accctggtag tccacgccgt aaacgatgag tgctaagtgt tggagggttt ccgcccttca gtgctgcagc aaacgcatta agcactccgc ctggggagta cgaccgcaag gttgaaactc aaaggaattg acgggggccc gcacaagcgg tgga
```

Many strains of Enterobacteriaceae and *Enterococcus* were able to grow on biomass, even cellulosic or lignocellulosic biomass, such as neutral detergent fiber (NDF), while also using gases from the headspace when the headspace included $H_2$ and $CO_2$ at greater than 1 atmosphere, and preferably with a ratio of $H_2$ to $CO_2$>1 (or 1:1), and more preferably greater than 2 (2:1) or 3 (3:1). For example, in one study twenty isolated organisms of various species cultured separately digested plant fiber (NDF) and used gas when incubated with $H_2$ and $CO_2$ in a ratio of 3:1 $H_2$:$CO_2$, and several produced more alcohols and acids when under pressure. When the same strains were incubated under the same conditions in another treatment except using only 1 atm $CO_2$ initially in the headspace (no added $H_2$), they produced gas and produced less acid and less alcohol. Therefore, organisms can simultaneously digest biomass and incorporate $CO_2$ under reducing conditions.

These examples show that many bacteria that use biomass can also ferment gases. If the gas pressures are increased, and particularly if the $H_2$ pressure increases, the fermentation shifts toward favoring these bacteria that make higher concentrations of alcohols or longer-chain VFA. Increasing the gas pressure in the fermenter above an atmosphere, and increasing the concentration of $H_2$ is a means to shift fermentation of plant biomass toward higher concentrations of longer chain VFA and alcohols in favor of acetate.

Process to Make Alcohols or Acids

The isolated microorganisms can be used in a process to make lower alkyl alcohol or organic acids or both. Some isolated microorganisms tolerate high concentrations of alcohol and shift fermentation exclusively toward alcohol when the alcohol concentration is high (e.g. >4% ethanol by volume). Some strains (e.g. *Klebsiella oxytoca*) mostly make alcohol and non-acid co-products. Since these organisms also grow rapidly under aerobic or anaerobic conditions from organic substrate, but only grow slowly from $CO_2$, CO and $H_2$; it may be advantageous to use two steps for production of alcohols or acids. In one step, the organism is grown to a desired population density; and in a separate anaerobic step, the alcohols or desired acids are produced. When co-products are produced along with the desired products, those co-products can be transferred to the step for growth of the organisms.

The slow growth from $CO_2$, CO and $H_2$ is advantageous because the products (alcohols and acids) are produced at very high conversion efficiency; a high percentage of the gases are converted to the desired organic compounds rather than to microbial cells. However, because of the slow growth during fermentation with gases, the microbial cells may need to be grown rapidly in a separate step. The fastest growth occurs during fermentation of organic products under aerobic conditions. For example, several species were found to use glucose, amino acids, volatile acids, or alcohols for growth. Using organic substrates, rather than gases, colonies formed on agar within 24 hours at 38° C.; or broth began to become cloudy within 24 h. After a few days of microbial growth, the medium becomes anaerobic. Then $CO_2$, CO, or an intermediate like $HCO_3^-$ and $H_2$ or an intermediate like $H_2S$ can be added to produce alcohols or acids. After production of the desired alcohol, the alcohol may be removed by distillation. Vacuum distillation (low pressure but moderate temperature such as less than 50° C.) can be used so that the microbial cells are not killed. Alternatively, the cells can be separated from the liquid by filtering or by embedding them on a fixed sheet before distillation of the separated liquid. Still another alternative is to leave the cells in the medium during distillation and later use the dead cells as substrate for additional microbial growth, or remove them and use them as an animal feed or other product. Once the alcohol or other product is removed from the liquid medium, the liquid can be used again to produce more alcohol. If necessary, the remaining organic products can be used as substrate to grow additional microbes possibly under aerobic or anaerobic conditions, or possibly starting under aerobic conditions that become more anaerobic.

The isolated and described microorganisms can allow many variations to the process. For example, fiber-digesting microbes can be used to produce alcohol or acids under conditions favoring their production. Strains of *Citrobacter koseri* can be used to produce ethanol, or other lower alkyl alcohol, or volatile fatty acid. *Citrobacter koseri* strains were known to be aerobic, alcohol tolerant, acid tolerant, to produce alcohol under anaerobic conditions, and to survive on medium with only citrate as the carbon source. The inventors discovered and isolated strains of *Citrobacter koseri* that produce alcohols, including ethanol, by fermenting $CO_2$ or CO as the only carbon source. Strains of *Klebsiella oxytoca* were known to be similar to *Citrobacter* except they do not produce very much organic acid, and therefore partition more of the fermentation gases to ethanol. *Escherichia coli* strains can also be used. These example strains show that it is feasible to produce alcohols by fermenting $CO_2$ or CO to ethanol or propanols or butanols under conditions in which it is thermodynamically feasible. Other strains of bacteria could also be used for the process, or other microorganisms including fungi could also be used in a similar way. The metabolism within these species is typically optimal at about 38° C., but they are still active above 20° C. Some strains grow and produce products optimally at 25° C., so the temperature would be adjusted depending on the strain.

CONCLUSIONS

One embodiment of this invention is an isolated facultative aerobic microorganism that uses carbon monoxide or carbon dioxide as a sole carbon source to produce a lower alkyl alcohol or organic acid. The lower alkyl alcohol produced may be ethanol, a propanol (e.g. 1-propanol or isopropanol), or a butanol (e.g. 1-butanol or iso-butanol). The organic acid may be: acetic acid, propionic acid, butyric acid, lactic acid, citric acid, malic acid, fumaric acid, succinic acid, or other acid. The isolated microorganism may be identified by having 16S rRNA that is at least 97% identical to a member of one of the genera: *Citrobacter, Klebsiella, Enterobacter, Salmonella,* or *Escherichia*. It may also be identified biochemically or phenotypically as a member of the genus *Citrobacter, Klebsiella, Enterobacter,* or *Escherichia*. The isolated microorganism is negative to Gram strain; it may be motile rods with peritricous flagella (e.g. *Citrobacter*). It may also be non-motile. The isolated microorganism may be further identified by its ability to grow in open air or anaerobically on medium containing citric acid as the only carbon source (*Citrobacter* or *Klebsiella*). It may also grow in air or anaerobically from glucose, lactic acid, or ethanol as the sole (only) carbon source.

The isolated microorganism may be identified by 16S rRNA as at least 97% identical to a member of *Citrobacter* genus, especially *Citrobacter koseri* or *Citrobacter* species MV6. The isolated micoorganism may be identified by 16S rRNA at least 97% identical to a member of *Escherichia* genus, especially *Escherichia coli*. It may also be identified as having 16S rRNA that is at least 97% homologous with a member of *Klebsiella* genus, especially *Klebsiella oxytoca*. The bacteria with greater than 97% identity to a member of the *Citrobacter* or *Klebsiella* genus are gram negative rods with ability to grow on citrate as the sole carbon source.

An additional embodiment of the invention is an isolated chemoautotrophic bacterium that grows on a single-carbon substrate, such as carbon monoxide or carbon dioxide as a sole carbon source. The isolated chemoautotrophic bacterium may be aerobic. The isolated chemoautotrophic bacterium comprises genes encoding enzymes for a metabolic pathway to produce a lower alkyl alcohol or an organic acid. The isolated chemoautotrophic bacterium additionally may comprise genes encoding enzymes for citric acid cycle, and at least some genes for the reverse citric acid cycle, or Woods-Ljungdahl pathway, or Calvin Cycle. For example, it may be a bacterium that has genes to encode a citrate lyase enzyme to cleave citrate to form acetylCoA and oxaloacetate. In one embodiment, the isolated chemoautotrophic bacterium is a member of Enterobacteriaceae family such as a member of a genus *Citrobacter, Klebsiella, Enterobacter,* or *Escherichia*, such as *Klebsiella oxytoca, Citrobacter koseri, Citrobacter* species MV6, or *Escherichia coli*.

One embodiment of the invention is an isolated microorganism that is chemoautotrophic, facultative aerobic, non-photosynthetic, grows on carbon monoxide or carbon dioxide as sole carbon source, and produces an organic product. The organism produces a lower alkyl alcohol and/or an organic acid, and is tolerant to at least 0.5%, 1%, 2%, 3%, 4%, 5%, 6%, or greater lower alkyl alcohol by volume, or alternatively is tolerant to as much as 1%, 2%, or 3% organic acids by volume at neutral pH. The isolated microorganism grows in a fermentation broth with 6% or greater lower alkyl alcohol concentration by volume, and can utilize the ethanol when it is thermodynamically feasible to obtain energy that way, or produce more ethanol above 6% under highly reducing conditions wherein it is thermodynamically feasible to produce more. The 16S rRNA from the isolated microorganism is at least 97% identical to a member of *Citrobacter* genus, *Klebsiella* genus, *Escherchia* genus. Another embodiment of the invention is a process to produce an organic product using the isolated microorganism herein described The invention also embodies a process to produce a lower alkyl alcohol or an organic acid from carbon dioxide or carbon monoxide comprising: a) an aerobic step wherein microorganisms grow from a carbon source that is degraded by microorganisms under aerobic conditions; and b) an anaerobic step wherein the lower alkyl alcohol or the organic acid is produced from carbon dioxide or carbon monoxide under anaerobic conditions. The lower alkyl alcohol or the organic acid may be removed from the culture. The microbial culture may comprise one species, or at least two or more species of microorganisms, and the microbial culture may comprise an aerobic and an anaerobic microorganism. An organism in the microbial culture may grow from carbon monoxide or carbon dioxide as a sole source of carbon. One species of microorganism may produce organic substrate or a growth factor used by another species of microorganism. Compounds produced during the anaerobic step may be consumed as organic substrate in the aerobic step. Preferably, desired products like alcohols or acids may be removed during or after the anaerobic step, and undesired residual products may be consumed during the aerobic step. A liquid, gas, or a nutrient may be recycled from step to step. In the anaerobic step, the lower alkyl alcohol concentration may reach greater than 2%, 3%, 4%, or 5% but preferably greater than 6% by volume. Additionally, a volatile fatty acid or other organic acid may be removed. The organic acid may be greater than 2%, 3%, or more by weight per volume of the fermentation broth. At least one species of microorganism in the culture may comprise a member of Enterobacteriaceae such as a member of the genera: *Citrobacter, Klebsiella, Enterobacter*, or *Escherichia* genus, such as a member of the species *Citrobacter koseri, Citrobacter* species MV6, *Escherichia coli*, or *Klebsiella oxytoca*. Exogenous hydrogen may be supplied. The temperature of the process may be between 20° C. and 60° C. or lower or higher. Preferably the temperature is between 35° C. and 45° C.

An additional embodiment of the invention is a composition of matter comprising a culture of microorganisms comprising an identified chemoautotrophic bacterium, such as a member of the family Enterobacteriaceae in an aqueous broth or agar media in a reactor vessel with CO, or $CO_2$ and $H_2$ gas under at least 1 atm pressure, and preferably under 2, or 4 atm pressure, and even more preferably under at least 8 atm pressure. Preferably, the ratio of $H_2$ to $CO_2$ is greater than 1:1 and even more preferably greater than 2:1 or 3:1. Preferably, the composition of matter comprises a member of one of the species: *Citrobacter koseri, Klebsiella oxytoca*, or *Escherichia coli*.

A further embodiment of the invention is a process to produce a multi-carbon organic product from a single-carbon substrate comprising the steps: a) culturing microorganisms comprising a chemoautotrophic bacterium that grows on a single-carbon substrate as sole carbon source in a fermentation broth in a reactor vessel with the single-carbon substrate and a reducing agent; b) supplying the single-carbon substrate and reducing agent to the reactor vessel; and c) the culturing and supplying steps causing the microorganisms to produce the multi-carbon organic product. The multi-carbon organic product may be an alcohol or acid, or other organic product. The single-carbon substrate may be CO, $CO_2$, $HCO_3^-$, formate or other single carbon compound. The reducing agent may be hydrogen, electricity from an electrode (e.g. a graphite or metal electrode), metal, or sulfur compound such as sulfide.

A further embodiment of the invention is a process to produce a lower alkyl alcohol or carboxylic acid from carbon dioxide or carbon monoxide comprising the steps: a) reduction of oxygen by a facultative aerobic microorganism; and b) synthesis by a microorganism of a multi-carbon compound from carbon dioxide or carbon monoxide. The same strain or consortium of microorganisms may be used in both steps "a" and "b". If a consortium of microorganisms is used, it may comprise both aerobic and anaerobic species. At least one of the microorganisms may include a chemoautotrophic organism, which may be a member of the Enterobacteriaceae family, such as a member of a genus *Citrobacter, Klebsiella*, or *Escherichia*. For example, *Citrobacter koseri, Klebsiella oxytoca*, or *Escherichia coli* may be used. An exogenous reducing agent may be added to the fermentation. For example, $H_2$ gas, sulfide, or CO gas may be the reducing agent. The concentration of lower alkyl alcohol may reach greater than 2% of broth volume, and preferably greater than 3%, or 4%, or more than 5% or 6% of fermentation broth volume.

A further embodiment of the invention comprises a method to isolate a chemoautotrophic bacterium that uses a single-carbon substrate to produce a multi-carbon organic product, said method comprising: a) growing a culture of microorganisms with the multi-carbon organic product under conditions wherein it is thermodynamically feasible to degrade the multi-carbon organic product, or alternatively under conditions to make more of the multi-carbon product from the single-product substrate; b) growing said culture of microorganisms under reducing conditions with the single-carbon substrate, preferably as the only source of carbon, or alternatively wherein both the single-carbon substrate and the multi-carbon product are provided but is thermodynamically favorable to produce more of the multi-carbon product; and c) isolating a microorganism that grows in both step "a" and step "b". Step b may include a reducing agent such as hydrogen gas, electrode with electrons, sulfide, or metal (Fe, Cu, Mn), or other reducing agent.

A further embodiment of the invention comprises a method to isolate a chemoautotrophic bacterium that uses carbon monoxide or carbon dioxide as a carbon source to produce a lower alkyl alcohol or organic acid, said method comprising: a) growing a culture of microorganisms with the lower alkyl alcohol or organic acid under conditions wherein it is thermodynamically feasible to degrade the lower alkyl alcohol or organic acid; b) growing said culture of microorganisms under anaerobic conditions with carbon monoxide or carbon dioxide as a source of carbon, preferably as the only source of carbon; and c) isolating a microorganism that grows in both step a and step b. Step b may include a reducing agent such as hydrogen gas, sulfide, or metal such as reduced iron or reduced copper. The lower alkyl alcohol may be ethanol, a propanol (e.g. 1-propanol, iso-propanol), or a butanol (e.g. 1-butanol, iso-butanol). The organic acid may be any of acetic acid, propionic acid, butyric acid, oxaloacetic acid, citric acid, malic acid, fumaric acid, or other acid. The carbon monoxide or carbon dioxide may be the sole source of carbon in step b.

A method was described and enabled to isolate an aerobic microorganism that grows on carbon monoxide or carbon dioxide as a sole carbon source, and produces a lower alkyl alcohol or organic acid, said method comprising: a) growing a culture of microorganisms with the lower alkyl alcohol or organic acid under aerobic conditions; b) growing the culture of microorganisms under reducing conditions with carbon monoxide or carbon dioxide as a sole carbon source; and c) isolating a microorganism that grows in the aerobic and reducing conditions. An exogenous reducing agent may be added to the culture to establish the reducing conditions. For example, reducing agents include $H_2$ gas or sulfide. The concentration of lower alkyl alcohol in step "a" may be greater than 0.5%, 1%, 2%, or 3%, by volume. The concentration of lower alkyl alcohol may also be greater than 4%, 5%, or 6% by volume. Thus, the isolated microorganism will be tolerant to the lower alkyl alcohol. The organic acid in step "a" may be any organic acid, for example, formic acid, or a $C_2$-$C_8$ organic acid, such as acetic, propionic, butyric, isobutyric, valeric, isovaleric, or longer acid.

Having described the present invention, it will be apparent that changes and modifications may be made to the above-described embodiments without departing from the sprit and the scope of the present invention.

All volumes and percentages related to alcohols are stated as volume/volume, unless stated otherwise or clearly contradicted by the context. For example, 5% ethanol means 5 ml of ethanol per 100 ml fermentation broth.

All percentage concentrations related to acids are stated as weight/volume and weight includes weight of both conjugate acid form and conjugate base form, unless stated otherwise. For example, 5% acetic acid means 5 grams acetic acid and acetate per 100 ml fermentation broth, with distribution of conjugate acid and conjugate base forms determined by pH.

All references, including publications, patent applications, patents, and website content cited herein are hereby incorporated by reference to the same extent as if each reference were individually and specifically indicated to be incorporated by reference and was set forth in its entirety herein.

The use of the terms "a" and "an" and "the" and similar referents in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Where ratios are expressed as single values (e.g. molar ratios or ratios of gas composition), it is intended to mean the value divided by 1. For example, the phrase "ratio of $H_2$ to $CO_2$ of at least 2" means 2 or more units of pressure of $H_2$ per unit of pressure of $CO_2$, or 2:1 or greater, such as 2.5:1 or 3:1, or 4:1.

The word "about," when accompanying a numerical value, is to be construed as indicating a deviation of up to and inclusive of 10% from the stated numerical value.

The use of any and all examples, or exemplary language ("e.g." or "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A process for producing a multi-carbon organic product from a single-carbon substrate comprising:
   a) transferring microorganisms to a fermentation broth in a reactor vessel, wherein said microorganisms comprise a member of the Enterobacteriaceae family;
   b) supplying the single-carbon substrate and a reducing agent or a compound that is both a single-carbon substrate and a reducing agent to the reactor vessel;
   c) culturing the microorganisms under conditions causing the microorganisms to produce the multi-carbon organic product from the single carbon substrate; and
   d) recovering the multi-carbon organic product from the reactor vessel.

2. The process of claim 1, wherein the single-carbon substrate comprises carbon dioxide.

3. The process of claim 1, wherein the multi-carbon organic product comprises a lower alkyl alcohol.

4. The process of claim 1, wherein the multi-carbon organic product comprises a carboxylic acid.

5. The process of claim 1, wherein the reducing agent comprises $H_2$ gas.

6. The process of claim 1, wherein the reducing agent comprises sulfide.

7. The process of claim 3, wherein volume of lower alkyl alcohol reaches at least 2% of broth volume.

8. The process of claim 3, wherein volume of lower alkyl alcohol reaches at least 6% of broth volume.

9. The process of claim 1, wherein the compound that is both a single-carbon substrate and a reducing agent is carbon monoxide.

10. The process of claim 1, wherein the member of the Enterobacteriaceae is from a genus *Escherichia, Proteus, Citrobacter, Klebsiella, Salmonella,* or *Enterobacter.*

11. The process of claim 10, wherein the *Escherichia* is *Escherichia coli.*

12. The process of claim 10, wherein the *Citrobacter* is *Citrobacter koseri* or wherein the *Klebsiella* is *Klebsiella oxytoca.*

13. The process of claim 3, wherein the lower alkyl alcohol comprises ethanol.

14. The process of claim 3, wherein the lower alkyl alcohol comprises a butanol.

15. A process for producing a multi-carbon organic product from a single-carbon substrate comprising:
   a) transferring microorganisms to a fermentation broth in a reactor vessel, wherein said microorganisms comprise an *Escherichia coli* strain;
   b) supplying the single-carbon substrate and a reducing agent or a compound that is both a single-carbon substrate and a reducing agent to the reactor vessel;
   c) culturing the microorganisms under conditions causing the microorganisms to produce the multi-carbon organic product; and
   d) recovering the multi-carbon organic product from the reactor vessel.

16. The process of claim 15, wherein the single carbon substrate comprises carbon dioxide and the reducing agent comprises hydrogen, and the multi-carbon organic product comprises a fatty acid, an alcohol or an alkane.

17. A process to convert carbon dioxide to a multi-carbon product comprising:
   a) transferring microorganisms to a fermentation broth in a reactor vessel, wherein said microorganisms comprise a member of the Enterobacteriaceae family that is selected or adapted to grow on carbon dioxide as a carbon substrate;
   b) supplying the carbon dioxide and a source of hydrogen to the reactor vessel;
   c) culturing the microorganisms under conditions causing the microorganisms to produce the multi-carbon product; and
   d) recovering the multi-carbon organic product from the reactor vessel.

18. The process of claim 17, wherein the multi-carbon product is an alcohol, a fatty acid, or an alkane.

19. The process of claim 1, wherein the member of the Enterobacteriaceae family has a natural capacity to convert a single-carbon substrate to a multi-carbon organic product.

* * * * *